US010739326B2

(12) United States Patent
Jacobi et al.

(10) Patent No.: US 10,739,326 B2
(45) Date of Patent: Aug. 11, 2020

(54) ANALYZING A ROCK SAMPLE

(71) Applicant: Saudi Arabian Oil Company, Dhahran (SA)

(72) Inventors: David Jacobi, Spring, TX (US); John Longo, Houston, TX (US); Jordan Kone, Deer Park, TX (US); Qiushi Sun, Houston, TX (US)

(73) Assignee: Saudi Arabian Oil Company, Dhahran (SA)

(*) Notice: Subject to any disclaimer, the term of this patent is extended or adjusted under 35 U.S.C. 154(b) by 162 days.

(21) Appl. No.: 15/977,496

(22) Filed: May 11, 2018

(65) Prior Publication Data

US 2018/0328905 A1 Nov. 15, 2018

Related U.S. Application Data

(60) Provisional application No. 62/506,263, filed on May 15, 2017.

(51) Int. Cl.
*G06K 9/00* (2006.01)
*G01N 33/24* (2006.01)
(Continued)

(52) U.S. Cl.
CPC ....... *G01N 33/241* (2013.01); *G01N 23/2251* (2013.01); *G06T 7/0008* (2013.01);
(Continued)

(58) Field of Classification Search
CPC combination set(s) only.
See application file for complete search history.

(56) References Cited

U.S. PATENT DOCUMENTS 6,140,643 A 10/2000 Brown et al.
8,101,907 B2 1/2012 Jacobi et al.
(Continued)

FOREIGN PATENT DOCUMENTS

CN 105 181 717 A 12/2015

OTHER PUBLICATIONS

Patel, Computer vision-based limestone rock-type classification using probabilistic neural network, 2014 (Year: 2014).*
(Continued)

*Primary Examiner* — Alex Kok S Liew
(74) *Attorney, Agent, or Firm* — Choate, Hall & Stewart LLP; Charles E. Lyon; Alexander D. Augst

(57) ABSTRACT

An example method includes analyzing rock from an image of a sample region of the rock. The example method includes accessing element maps of the sample region in a database, with each element map including an array of pixels, and with each pixel having a value that represents how closely the pixel correlates to a chemical element; accessing a database storing threshold values for multiple chemical elements including the chemical element; determining a presence of a substance in a portion of the sample region corresponding to the pixel by determining whether a value of the pixel in each of the element maps is greater than, or less than, a threshold value for a corresponding chemical element; labeling the pixel based on the presence of the substance in the pixel; and outputting data representing the substance map for rendering on a graphical interface.

39 Claims, 18 Drawing Sheets

(51) Int. Cl.
*G01N 23/2251* (2018.01)
*G06T 7/00* (2017.01)
*G01N 23/223* (2006.01)
*G01N 23/20091* (2018.01)
*G01N 23/2209* (2018.01)
*G01N 23/2206* (2018.01)

(52) U.S. Cl.
CPC ..... *G01N 23/20091* (2013.01); *G01N 23/223* (2013.01); *G01N 23/2206* (2013.01); *G01N 23/2209* (2018.02); *G01N 2223/616* (2013.01); *G06T 2207/10061* (2013.01)

(56) References Cited

U.S. PATENT DOCUMENTS

| | | | | |
|---|---|---|---|---|
| 9,507,047 | B1* | 11/2016 | Dvorkin | G01N 23/046 |
| 2010/0198638 | A1* | 8/2010 | Deffenbaugh | G01V 11/00 |
| | | | | 705/308 |
| 2013/0301794 | A1* | 11/2013 | Grader | G01N 23/087 |
| | | | | 378/5 |
| 2015/0262400 | A1 | 9/2015 | Howell et al. | |
| 2016/0093094 | A1* | 3/2016 | Walls | G06T 15/08 |
| | | | | 382/109 |
| 2017/0017011 | A1* | 1/2017 | Howard | G01N 15/088 |

OTHER PUBLICATIONS

International Search Report for PCT/US2018/032188, 5 pages (dated Sep. 21, 2018).
Written Opinion for PCT/US2018/032188, 7 pages (dated Sep. 21, 2018).
Bornstein, B. et al., Onboard detection of jarosite minerals with applications to Mars, IEEE Aerospace Conference, Paper #1513, Version 2: 7 pages (2006).
Gu, Y., Automated Scanning Electron Microscope Based Mineral Liberation Analysis, An Introduction to JKMRC/FEI Mineral Liberation Analyser, Journal of Minerals & Materials Characterization & Engineering, 2(10):33-41 (2003).
Harman, E.M. et al., Toward the Development of Automated Mineral Identification with the Zeiss Mineralogic Platform for the Routine Analysis of Mineral Exploration Samples by Laser Ablation Inductively-Coupled-Plasma Mass Spectrometry, 38th Annual Meeting of the Mineral Deposits Studies, p. 48 (2014).

* cited by examiner

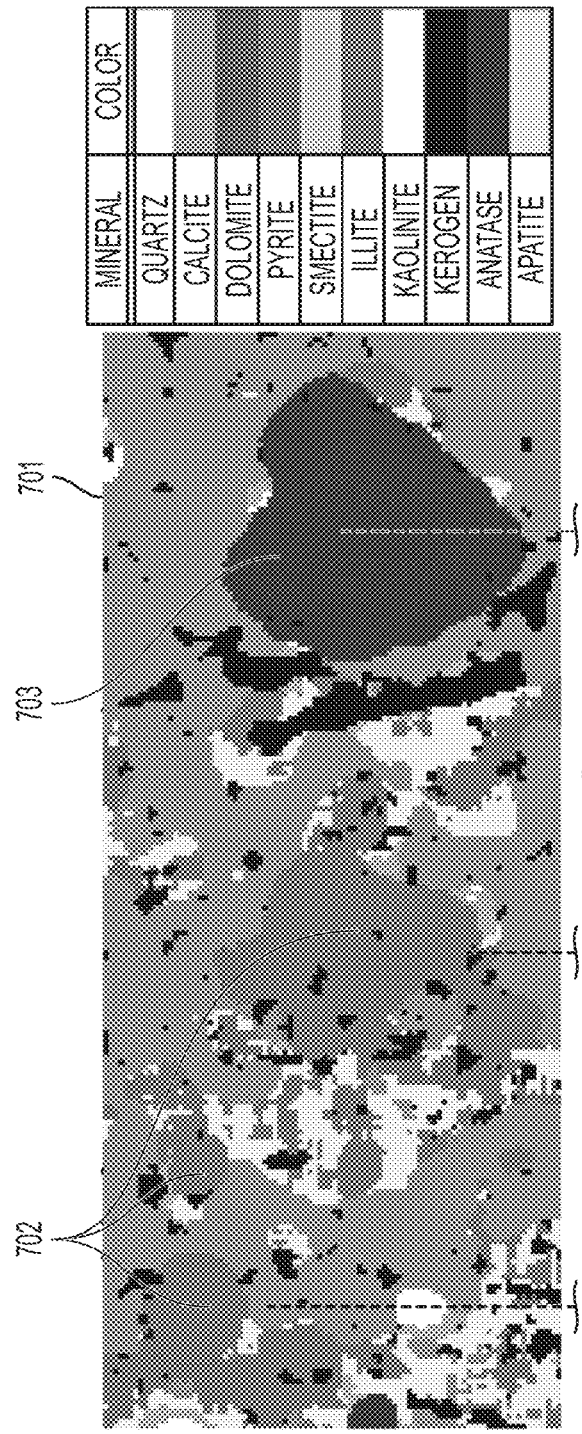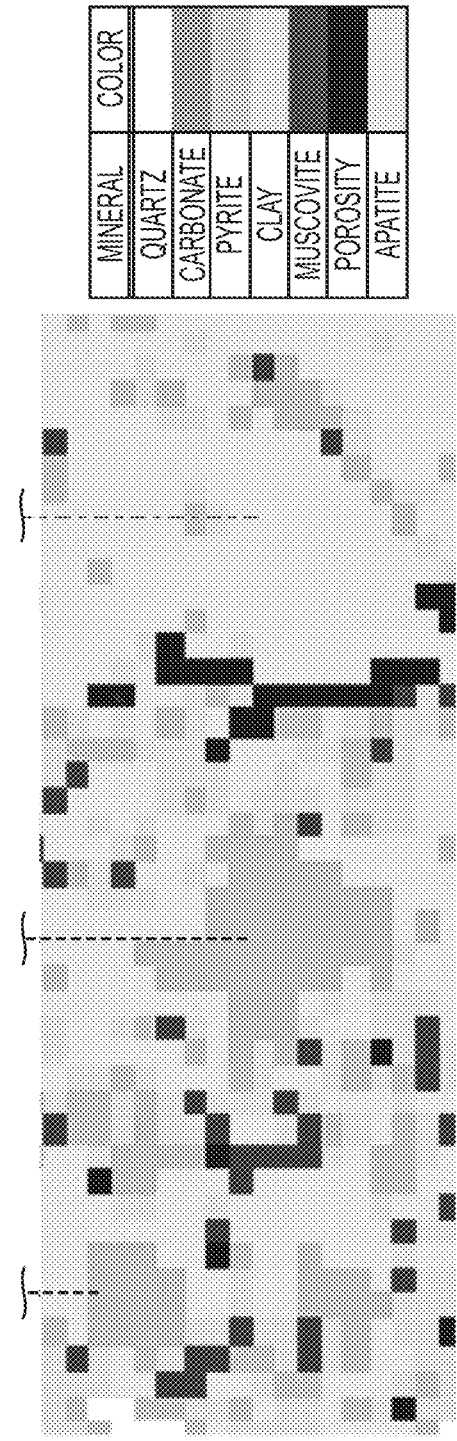
FIG. 7A
FIG. 7B

ANALYZING A ROCK SAMPLE

CROSS-REFERENCE TO RELATED APPLICATIONS

This application claims the benefit of U.S. Provisional Patent Application Ser. No. 62/506,263, filed May 15, 2017, entitled "Analyzing a Rock Sample," the disclosure of which is incorporated herein by reference in its entirety.

TECHNICAL FIELD

This specification describes example processes for analyzing rock samples, and for outputting images based on the analyses.

BACKGROUND

Rock may contain hydrocarbons, such as oil or gas. Criteria used to estimate the existence and amount of hydrocarbons in rock include, for example, the types of chemical elements or minerals in the rock and the quantities of those chemical elements and minerals in the rock. To determine the existence and amount of organic material, such as hydrocarbons or kerogen, in rock, imaging techniques may be used to capture images of the rock. The resulting images can be analyzed to identify the existence, and amounts, of organic material in the rock.

SUMMARY

This specification describes example processes that use geochemical relationships to determine a probable mineralogy, per pixel, of an image of a rock sample. Examples of types of images that may be analyzed to determine the probable mineralogy include, but are not limited to, images acquired using scanning electron microscopy (SEM). These images integrate elemental data and "Z" values measured and acquired using, for example, energy dispersive spectroscopy (EDS), back scatter electron (BSE) images, or wave dispersive spectroscopy (WDS). The output generated by the example processes may include a two-dimensional (2D) mineral map. This mineral map may be used for mineralogical assessments or for constructing three-dimensional (3D) focused ion beam-scanning electron microscope (FIB-SEM) sections. The mineral map may improve the ability to quantify reservoir properties for hydrocarbons. The example processes may also be used to quantify minerals in the rock sample using micro-X-ray fluorescence (micro-XRF) and may be used in combination with other techniques, such as Fourier transform infrared spectroscopy (FTIR).

In some implementations, mineral maps obtained using the example processes have resolutions, and quantifications of rock matrices, that are at the nano-scale. In some implementations, nano-scale may include pixels smaller than one micrometer ($\mu$m).

An example method comprises analyzing rock from an image of a sample region of the rock. The example method comprises accessing element maps of the sample region in a database, with each element map comprising an array of pixels, and with each pixel having a value that represents how closely the pixel correlates to a chemical element; accessing a database storing threshold values for multiple chemical elements including the chemical element; determining a presence of a substance in a portion of the sample region corresponding to the pixel by determining whether a value of the pixel in each of the element maps is greater than, or less than, a threshold value for a corresponding chemical element; labeling the pixel based on the presence of the substance in the pixel; and outputting data representing the substance map for rendering on a graphical interface. The example method may include one or more of the following features, either alone or in combination.

The image may be obtained using scanning electron microscopy (SEM). At least one element map may be generated based on a back scatter electron (BSE) image, an energy dispersive spectroscopy (EDS) image, a wave dispersive spectroscopy (WDS), or micro-X-ray fluorescence (micro-XRF) image. Each element map may be based on unprocessed image data. The chemical element may comprise at least one of: aluminum, calcium, carbon, chlorine, iron, oxygen, potassium, phosphorous, magnesium, sulfur, sodium, silicon, or titanium. A resolution of the substance map may be less than, or equal to, 250 nm per pixel.

Determining the presence of a substance in the portion of the sample region may comprise selecting an element map for a chemical element; comparing a value of the pixel in the element map to a first threshold; and detecting the presence of a substance by determining if the value of the pixel has a predetermined relationship with the first threshold. If the value of the pixel does not have the predetermined relationship with first threshold, the method further comprises repeating selecting, comparing, and determining for a different chemical element.

The predetermined relationship may comprise the value of the pixel being greater than the first threshold, or the value of the pixel being less than the first threshold.

The method may comprise selecting an element map for a first chemical element; comparing a value of the pixel in the element map to a first threshold; determining that the value of the pixel has a first predetermined relationship with the first threshold; selecting an element map for a second chemical element; comparing a value of the pixel in the second element map to a second threshold; determining that the value of the pixel has a second predetermined relationship with the second threshold; and labeling the pixel as a substance based on the value of the pixel having the first predetermined relationship with the first threshold and based on the value of the pixel having the second predetermined relationship with the second threshold.

The substance may be a mineral, and the substance map may be a mineral map.

The method may comprise receiving data representing the sample region, with the data being received from an imaging device and with the data representing the pixel at a nano-scale resolution. Determining the presence of a substance in the portion of the sample region may be based on the data received. The substance map may be at a resolution that is based on the nano-scale resolution. The method may comprise performing an assessment of substances in the substance map; and outputting data that is based on the assessment. The data that is based on the assessment may comprise a characterization of substances in the substance map. The method may further comprise determining a likelihood of hydrocarbons in the rock sample based on the characterization of the substances; and affecting operation of a hydrocarbon extraction process based on the likelihood of hydrocarbons in the rock sample.

Any two or more of the features described in this specification, including in this summary section, may be combined to form embodiments not specifically described in this specification.

All or part of the methods, systems, and techniques described in this specification may be implemented as a computer program product that includes instructions that are stored on one or more non-transitory machine-readable storage media, and that are executable on one or more processing devices. Examples of non-transitory machine-readable storage media include, for example, read-only memory, an optical disk drive, memory disk drive, random access memory, and the like. All or part of the methods, systems, and techniques described in this specification may be implemented as an apparatus, method, or system that includes one or more processing devices and memory storing instructions that are executable by the one or more processing devices to perform the stated operations.

The details of one or more implementations are set forth in the accompanying drawings and the description. Other features and advantages will be apparent from the description and drawings, and from the claims.

DESCRIPTION OF THE DRAWINGS

FIG. 7A shows a refined version of the mineral map shown in FIG. 6B; and FIG. 7B shows an example low-resolution version of the mineral map shown in FIG. 6B.

DETAILED DESCRIPTION

Figure 1:
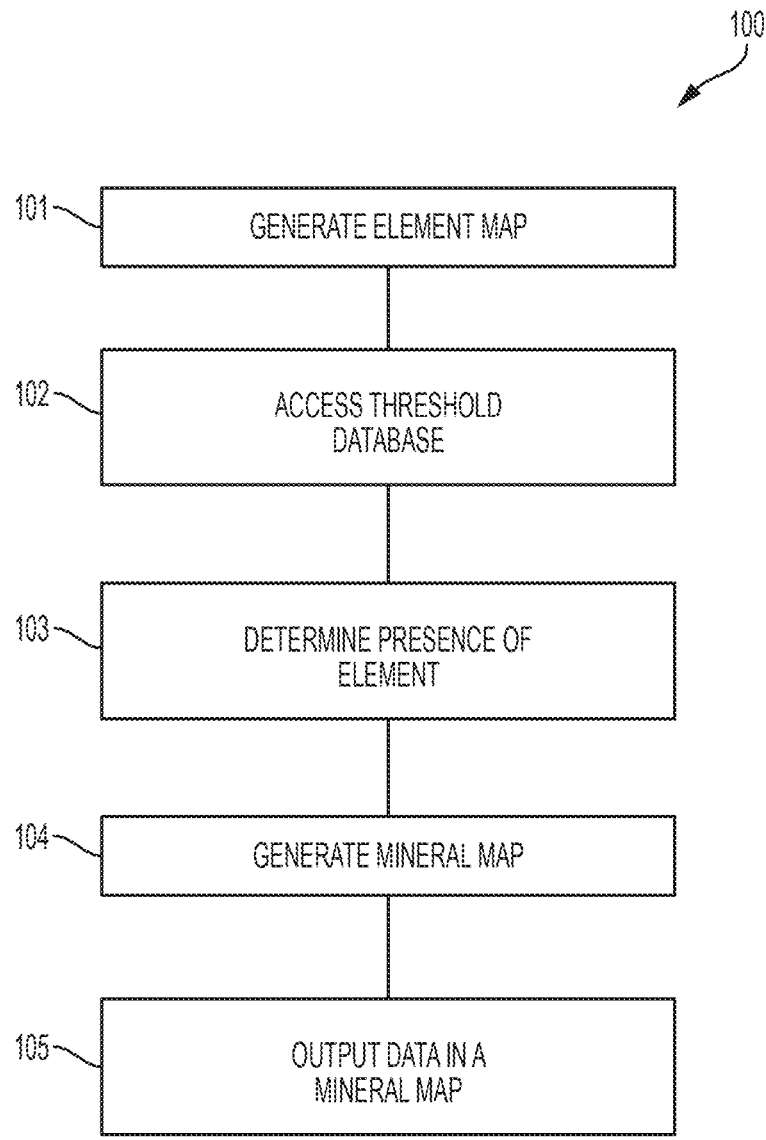
FIG. 1 shows an example process for generating a mineral map.

This disclosure includes example processes ("the processes") for generating pixel maps of structures, such as rocks or minerals. In an example process, an image of a rock is captured. The pixels in the image are at a nano-scale resolution. In some implementations, nano-scale resolution images may include pixels with a length of an edge smaller than one micrometer ($\mu m$), for example 250 nanometers (nm). Each individual pixel of the image is analyzed to determine the chemical composition of the part of the rock that the pixel represents. Based on this analysis, the process determines the mineral composition of the part of the rock. Because the process performs the analysis at a nano-scale resolution, it may be possible to generate pixel maps that are more detailed than those that are generated using lower-resolution images.

Technologies that the example processes may employ include, but are not limited to, SEM imaging techniques, including FIB-SEM, EDS, BSE, and WDS. In an example, SEM includes scanning (or exciting) the surface of a sample using a focused beam of electrons, and generating an image based on the signals caused by excitation of the surface. In an example, FIB-SEM includes a system that is based on a working principle similar to SEM, but that uses a focused beam of ions instead of electrons to excite a sample. In an example, EDS includes detecting and measuring the characteristic X-ray excitation (photons) of a sample. Because each chemical element has a unique atomic structure, a unique set of peaks on the electromagnetic emission spectrum for each sample element can be detected. In an example, WDS includes detecting X-rays from different elements and separating them using characteristic diffraction patterns of an element (called Bragg diffraction). In an example, BSE includes detecting electrons reflected from a sample. There is a close relation between a BSE signal and the atomic number (the "Z" value): heavier chemical elements scatter the beam electrons more strongly than light elements. In a BSE image, heavier elements may appear brighter than lighter elements.

Mineralogy is used in the oil and gas industry to estimate the quality and quantity of rock deposits including, but not limited to, hydrocarbon deposits. For example, the mineralogy of shale is indicative of its susceptibility to (hydraulic) fracturing (also known as "fracking"). Analysis of shale with methods such as petrographic sections may be challenging because shale is largely composed of relatively fine grained minerals. High-resolution imaging techniques, such as SEM, can be useful to obtain qualitative, topological, and quantitative information from shale or other rock samples. For example, high-resolution imaging techniques enable imaging, at sub-micron resolutions, of mineral grain boundaries and distribution in organic matter, such as kerogen. Such imaging may allow for enhanced two-dimensional (2D) mineralogical mapping and three-dimensional (3D) reconstruction of rock segments from images, such as FIB-SEM images. Sub-micron resolution of mineral grain boundaries may enable a relatively detailed determination of mineralogy, lithology, organic geochemistry and petrophysics in a sample, such as a shale sample.

In some examples, the processes use elemental data and gray-scale image data to identify or to quantify, or both, minerals, organic matter, or both minerals and organic matter, per pixel within an SEM/EDS image alone or in combination with a BSE image. FIG. 1 shows an example implementation of a process 100 for analyzing a rock sample from a microscopic image of a sample region of the rock sample. According to process 100, element maps for a rock sample are generated (101) by analyzing the rock sample using an EDS analysis, a WDS analysis, or both. In some implementations, an element map includes an array of pixels. Each pixel in the array has a gray-scale value that corresponds to the intensity of an EDS, WDS or BSE signal for a specific element. In this regard, because a rock sample may contain more than one element, multiple element maps may be generated for the same rock sample. Each element map may include the same pixel-by-pixel correlation between the element map and content of the rock sample such that the same pixel, from different element maps, may be analyzed to determine if that pixel represents one or more different chemical elements. The element maps may be stored in one or more appropriate databases or other storage constructs.

Figure 16:
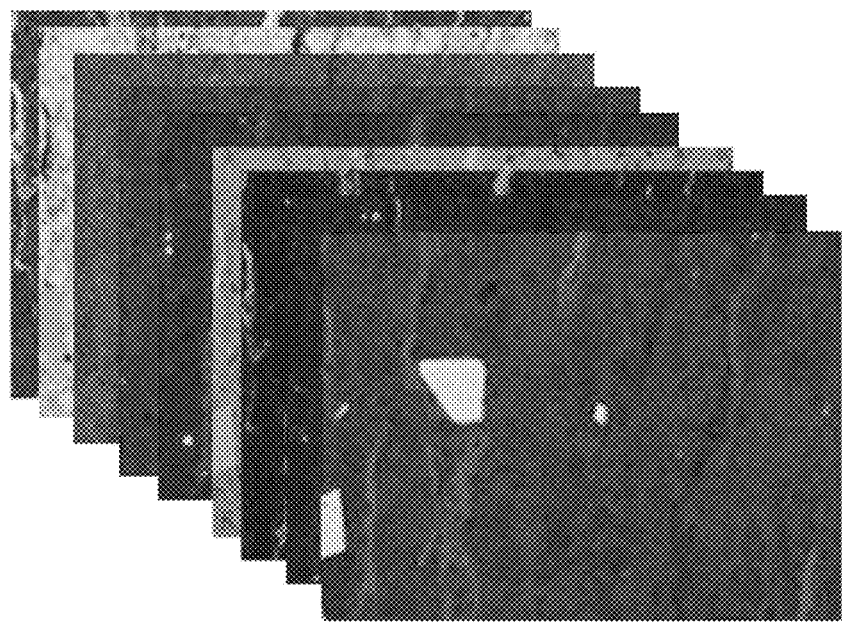
FIG. 16 shows a graphical representation based on the images shown in FIG. 15A and FIG. 15B.

In some implementations, to facilitate the determination of a rock sample's mineralogy, all element maps are loaded into a tensor model, in which the maps are configured as stacked pages. A corresponding BSE image may be added to help determine organics and porosity. FIG. 16 shows a graphical representation of an example data set.

To organize the image data, a three-index system may be used. The first two indices represent a spatial location of a pixel on the image in the form of [row, column]. The third index may be a depth index that reads the values of all the elemental maps. Thus, using a three-index system, any pixel in the stack can be located. If an XY location in the tensor model is called, the process returns an "elemental vector" containing all the values of the pixels at the specified location. This allows comparison of all the elements concurrently, in some cases.

In some implementations, each element map includes an array of pixels, and each pixel has a value that represents how closely that pixel is representative of a chemical element. For example, that value may be a gray-scale value, for example, between 0 and 255, that is greater or lesser than a pre-determined threshold value for that element. Process 100 accesses (102) a database to obtain the threshold values for chemical elements of selected element maps. Process 100 accesses, and selects, element maps and corresponding threshold values for a set of chemical elements. The chemical elements for which the threshold values and elements maps may be selected may be any appropriate set of pre-defined chemical values. For example, a user may have a list of chemical values for which the users wishes to test.

In this regard, because minerals have characteristic elemental compositions, a strong presence of certain elements that constitute a specific mineral can be detected. A threshold value can be established for each element. Each element responds differently to an electron beam excitation in EDS, so thresholds may not be universal between elements. For example, a value of "80" for iron may not mean the same as a value of "80" for titanium. Thresholds to determine a Boolean variable that would indicate the presence, or absence, of an element are established. In some implementations, by looking for the most characteristic minerals first, parameters may be tested sequentially in order to determine the mineralogical composition of a sample of rock represented by a pixel under consideration.

Figure 2:
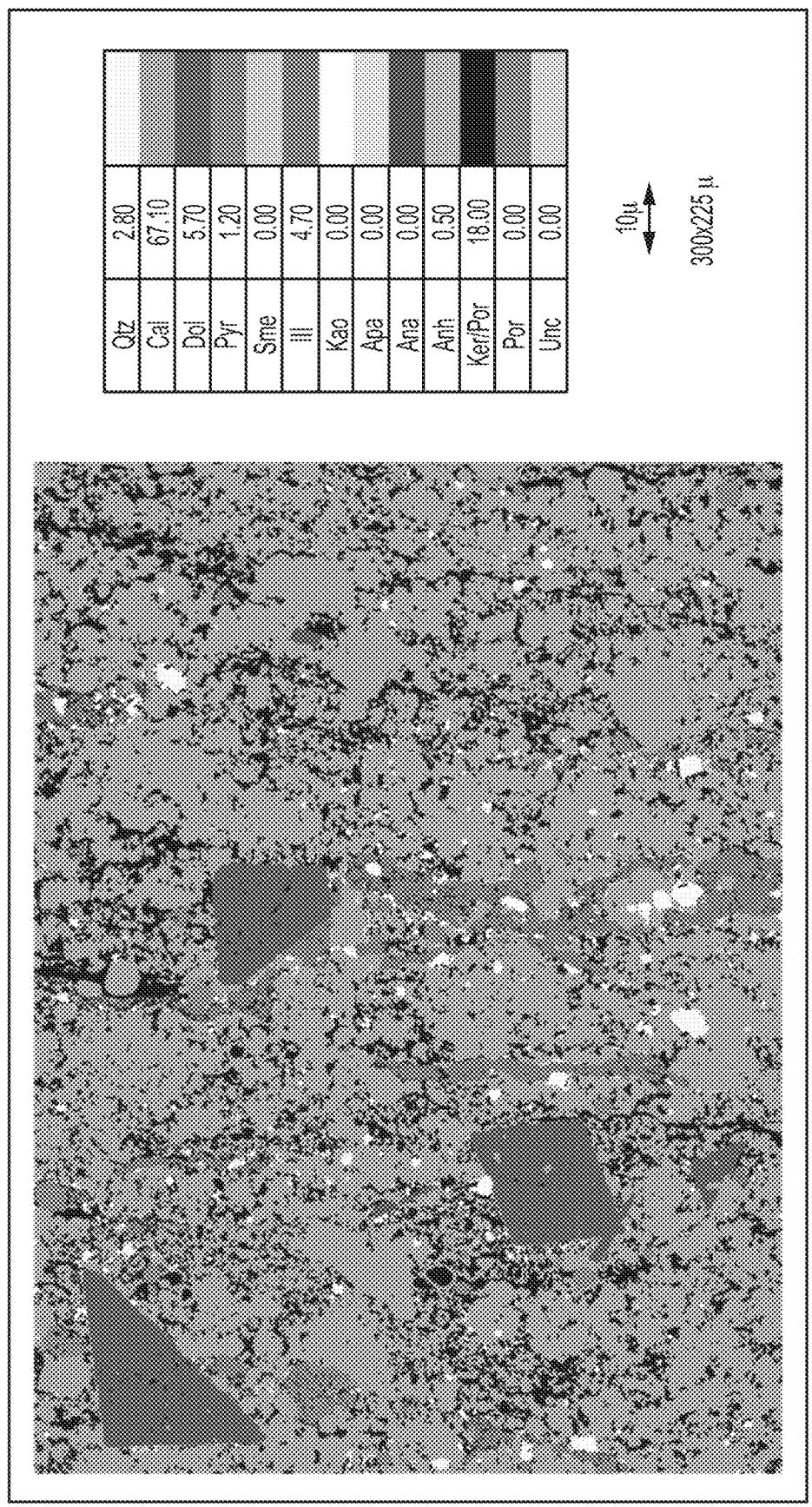
FIG. 2 shows an example mineral map.

In some implementations, the selected element maps contain data representing the compositions of sedimentary rocks, although other types of maps may be selected. That data may be used to determine a probable mineralogy of the rock sample from SEM-derived EDS or BSE images, or both. For example, the data may be used to generate a substance map, such as a mineral map, showing the distribution of substances, such as minerals, and the amounts of those substances—again, such minerals—present in the rock sample. An example of a mineral map generated by the example processes is shown in FIG. 2. In some implementations, the distribution and amount of minerals present in the rock sample may be expressed in weight percent (wt %) or volume percent (vol %) of the minerals relative to the overall sample. To determine a probable mineralogy of a rock sample, the process obtains threshold values from the database for chemical elements from the element maps.

Figure 3:
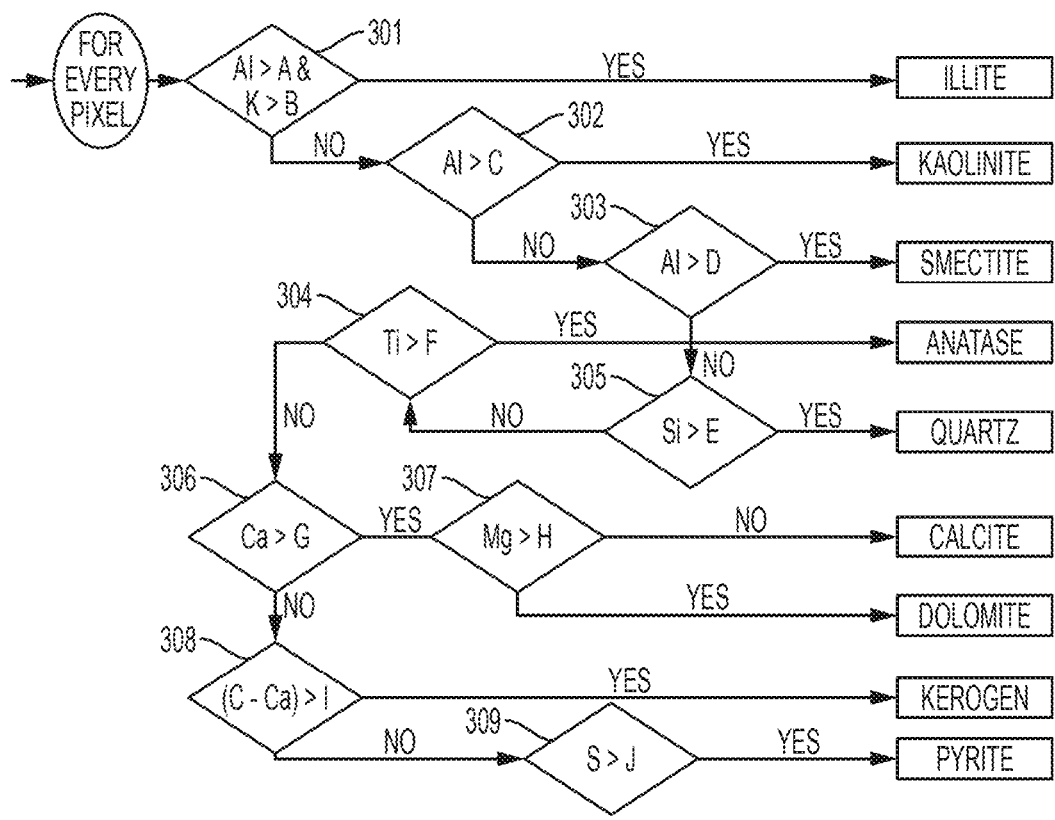
FIG. 3 is a flowchart showing an example process for performing a mineralogical analysis.
Figure 4:
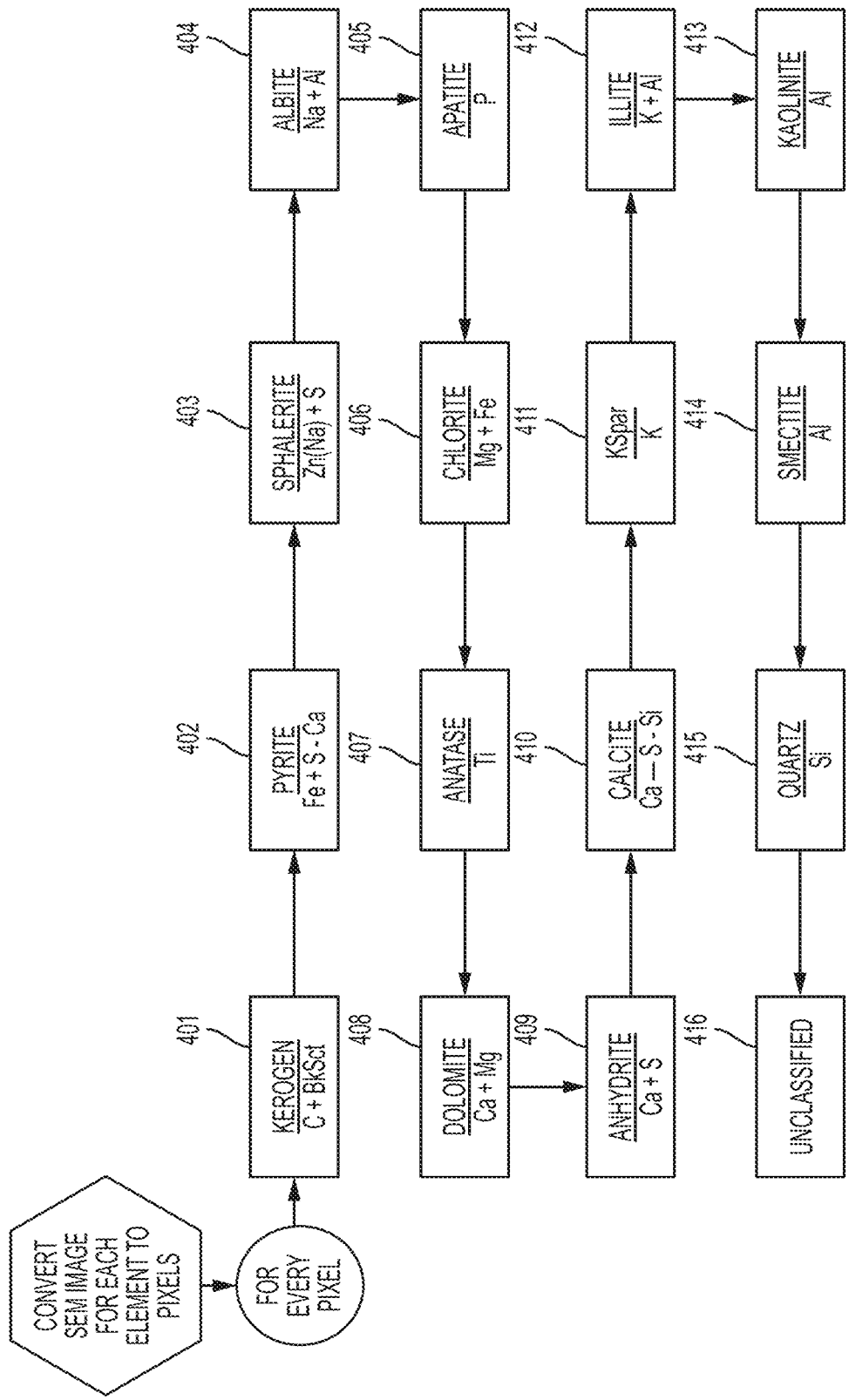
FIG. 4 is a flowchart showing an example process for performing a mineralogical analysis.

Process 100 uses the obtained thresholds to determine (103) a presence of a substance, such as a mineral or organic material, in the rock sample. In some implementations, process 100 makes this determination by analyzing an image, such as an SEM image, of the rock sample on a pixel-by-pixel basis. FIGS. 3 and 4 show example processes for performing such an analysis. However, analyses other than those shown in FIGS. 3 and 4 may be performed. In some implementations, the analysis may include comparing values of the same pixels from different element maps to thresholds for each of a set of chemical elements, and determining whether a predefined relationship to the threshold is present for each chemical element. For example, the predefined relationship may include that the value exceeds the threshold or that the value is less than the threshold. Whether or not the chemical element is present in a part of the rock sample is determined based on whether the pixel value representing that part of the rock sample is greater or less than the threshold for that chemical element.

Based on the presence or absence (103) of a chemical element in the rock sample, process 100 generates (104) data representing a mineral map for the rock sample. In some implementations, the mineral map includes information representing the content of the rock sample. The mineral map may represent different minerals using different colors, textures, or other appropriate distinguishing indicia. As explained before, in some implementations, mineral maps generated using process 100 have resolutions, and quantifications of rock matrices, that are at the nano-scale. In some implementations, nano-scale may include pixels smaller than one micrometer (μm). In some implementations, mineral maps generated using process 100 may have resolutions, and quantifications of rock matrices, that are greater than a nano-scale or that includes pixels smaller than one micrometer (μm).

Process 100 outputs (105) data representing the mineral map for use in rendering the mineral map on an appropriate graphical user interface, such as, but not limited to, a computer monitor, or the screen of a tablet computer or smartphone. The mineral map is rendered, based on the data, by an appropriate graphical processing device for display to a user.

In some implementations of process 100, EDS and BSE data is collected, for example using SEM. This data is processed to obtain element information, such as raw elemental (spectral) data. The extracted and processed data may be used to generate the element maps described previously. In some implementations of the example processes, including process 100, data for each individual pixel is not converted to a chemical composition and subsequently matched to a minerals database. Instead, in some implementations, the example processes use raw elemental (spectral) data or other raw output data from an electron or X-ray detector of an SEM system. In some implementations, as noted, the raw output data may be normalized on a scale of, for example, 0 to 255. In some implementations, a graphical user interface (GUI) may be used to implement a real-time adjustment of the data's acquisition parameters to provide geologically consistent mineral maps. In some implementations, the acquisition parameters for the SEM system include the example settings shown in Table 1.

TABLE 1

| | |
|---|---|
| Accelerating voltage: | 15 kV (15,000 Volts) |
| Current | −2.5 nA (nano Amps) |
| Vacuum Pressure | 40 Pascals |
| Working Distance | 10.1 mm (millimeters) |
| Aperture | 120 μm (micro-meters) |
| Detectors used | Electron Backscatter and Secondary Electron |
| Map size | 300 μm × 225 μm |
| Counts | 100,000 cps (Counts per Second) |
| Image filter | Average filter of 5 |
| Colors Maps | Gray-scale 0-255 |
| Acquisition Time | 30 minutes |

By adjusting the acquisition parameters, images can be obtained that have relatively smooth circular shapes for pyrite framboids, and images can be obtained of diagenetic dolomite crystals that are relatively sharp-edged rhomboids. In some implementations, this information can be useful for characterizing a rock sample since, for example, shape and orientation of pyrite framboids or dolomite rhomboids can indicate when and how the surrounding rock was formed. In this regard, accurate morphology may help to differentiate minerals visually. In addition, clearly defined boundaries, and thus surface area, of each mineral may increase quantitative and qualitative accuracy. The visual results, obtained from the combination of the relatively high-resolution imaging and parameter flexibility facilitate accurate determinations of the chemical composition, and thus the minerals, of a rock sample. In some implementations, for an SEM image with approximately 750,000 pixels, a sufficiently large number of determinations may be made to ensure a statistically-correct overall mineral composition for a rock sample under consideration. The results may be displayed in a relatively high-resolution mineral map.

In some implementations, process 100 includes a "rules-based" process to determine mineralogy on a pixel-by-pixel basis. In some implementations, the pixels are on a nanoscale, which may result in a mineral map having relatively high resolution. Because the computation time for such a process is proportional to the number of pixels, larger images can, in some cases, take a longer time to process. To reduce the amount of processing time, the process may be automated to operate in response to a single command. In an example implementation, the example process may be implemented using MATLAB® produced by Mathworks® of 1 Apple Hill Drive, Natick, Mass.

As explained previously, process 100 uses thresholds to determine (103) a presence of a substance, such as a mineral or organic substance, in a rock sample. FIG. 3 shows an example process for analyzing a rock sample to make this determination. In the example of FIG. 3, values for one or more elements of interest are obtained from SEM data. These values correspond to how closely a pixel corresponds to a chemical element. In this regard, each element value of a pixel in an SEM element map corresponds to the presence of that element in the sample area represented by the pixel. In an example, an element value corresponds to an image gray-scale value that is normalized on a scale from 0 to 255. These element values can be used as inputs for use in analyzing element values in relation to a set of threshold values, examples of which are referred to as A, B, C, D, E, F, G, K, and J. In an example, the process of FIG. 3 performs an assessment of aluminum (in relation to threshold "A") and potassium (in relation to threshold "B") to determine whether the presence of illite is probable (301). In some implementations, the presence of a mineral is deemed probable if the comparison indicates a predefined relationship between the element value of the pixel and a threshold. For example, the presence of a mineral may be deemed probable if the element value is greater, or less than, the threshold value.

Continuing on with the FIG. 3 analysis, if aluminum and potassium are each less than a certain threshold value, then aluminum (in relation to thresholds "C" & "D") is considered to determine whether the pixel value corresponds to kaolinite (302) or smectite (303). If these criteria are not met, then silicon (in relation to threshold "E") followed by titanium (in relation to threshold "F") are evaluated to determine whether quartz (305) or anatase (304) is probable. If neither element meets the threshold criterion, then calcium (in relation to threshold "G") and magnesium (in relation to threshold "H") are considered to determine whether the pixel represents calcite (306) or dolomite (307). If the mineral is determined to be neither calcite nor dolomite, then the difference between carbon and calcium (in relation to threshold "I") intensity values provides a pathway to select either kerogen (308) or, upon evaluation of sulfur (in relation to threshold "J"), pyrite (309). The minerals and chemical compositions of FIG. 3 are examples, and other minerals and chemical compositions may be used in other implementations.

In an example implementation of the FIG. 3 process, example threshold values for each element are in Table 2.

TABLE 2

| | |
|---|---|
| A | 26 |
| B | 60 |
| C | 50 |
| D | 35 |
| E | 22 |
| F | 85 |
| G | 20 |
| H | 30 |
| I | 35 |
| J | 15 |

As explained previously, in some implementations, each threshold value may be, for example, a gray-scale value between 0 and 255. These values may be chosen or adjusted based on factors such as a maximum intensity, a minimum intensity, or an average intensity of pixel data that is representative of a particular element in an EDS or BSE image. Other threshold values can be used, as appropriate. In addition or in the alternative, other elements and minerals can be used with the example process of FIG. 3, examples of which include, but are not limited to, aluminum, calcium, carbon, chlorine, iron, oxygen, potassium, phosphorous, magnesium, sulfur, sodium, silicon, and titanium.

As explained previously, process 100 uses thresholds to determine (103) a presence of a substance, such as a mineral or organic substance, in a rock sample. FIG. 4 shows an example process for analyzing a rock sample to make this determination. In the example process of FIG. 4, values corresponding to the presence of one or more elements in pixels of interest are obtained from appropriate image data, such as SEM image data. The values may be intensity values, which represents how closely a pixel correlates to a chemical element. For example, the greater the intensity value is for a particular chemical element, the more likely it is that a sample of the rock represented by that pixel contains that chemical element. These values can be used to analyze the sample to determine the mineralogical composition of the sample. An example set of threshold values (also called parameters) that may be used with the process of FIG. 4 is shown in Table 3. In some implementations, the determination of the presence of a specific mineral is based on the analysis of more than one element, for example an analysis of two, three, or more elements. Accordingly, example parameters 1, 2, and 3 are shown in Table 3 for different example elements.

TABLE 3

| Mineral | Parameter 1 | Parameter 2 | Parameter 3 |
|---|---|---|---|
| Kerogen | BS < 50 | C > 20 | |
| Pyrite | Fe > 50 | S > 40 | Ca < 100 |
| Sphalerite | Zn > 100 | S > 50 | |
| Albite | Na > 100 | Al > 60 | |
| Apatite | P > 100 | | |
| Chlorite | Fe > 65 | Mg > 50 | |
| Anatase | Ti > 100 | | |
| Dolomite | Mg > 100 | Ca > 80 | |
| Anhydrite | Ca > 50 | S > 90 | |
| Calcite | Ca > 100 | S < 80 | Si < 100 |
| K-Spar | K > 100 | | |
| Illite | K > 30 | Al > 50 | |
| Kaolinite | Al > 80 | | |
| Smectite | Al > 50 | | |
| Quartz | Si > 20 | | |

In this example, the process of FIG. 4 performs an assessment of a BSE image, followed by an analysis of EDS Data. If a pixel of the BSE image has a gray-scale value less than a threshold value, and if the corresponding pixel of an element map for calcium has a value greater than a certain threshold value, the pixel of the mineral map is labeled as organics/pore (401). If the corresponding pixel of an element map for iron has an element value greater than a certain threshold value, and if the corresponding pixel of an element map for sulfur has an element value greater than a certain threshold value, and if the corresponding pixel of an element map for calcium has an element value smaller than a certain threshold value, the pixel of the mineral map is labeled as pyrite (402). If the corresponding pixel of an element map for zinc has an element value greater than a certain threshold value, and if the corresponding pixel of an element map for sulfur has an element value greater than a certain threshold value, the pixel of the mineral map is labeled as sphalerite (403). If the corresponding pixel of an element map for sodium has an element value greater than a certain threshold value, and if the corresponding pixel of an element map for aluminum has an element value greater than a certain threshold value, the pixel of the mineral map is labeled as albite (404). If the corresponding pixel of an element map for phosphorus has an element value greater than a certain threshold value, the pixel of the mineral map is labeled as apatite (405). If the corresponding pixel of an element map for iron has an element value greater than a certain threshold value, and if the corresponding pixel of an element map for magnesium has an element value greater than a certain threshold value, the pixel of the mineral map is labeled as chlorite (406). If the corresponding pixel of an element map for titanium has an element value greater than a certain threshold value, the pixel of the mineral map is labeled as anatase (407). If the corresponding pixel of an element map for magnesium has an element value greater than a certain threshold value, and if the corresponding pixel of an element map for calcium has an element value greater than a certain threshold value, the pixel of the mineral map is labeled as dolomite (408). If the corresponding pixel of an element map for calcium has an element value greater than a certain threshold value, and if the corresponding pixel of an element map for sulfur has an element value greater than a certain threshold value, the pixel of the mineral map is labeled as anhydrite (409). If the corresponding pixel of an element map for calcium has an element value greater than a certain threshold value, and if the corresponding pixel of an element map for sulfur has an element value smaller than a certain threshold value, and if the corresponding pixel of an element map for silicon has an element value smaller than a certain threshold value, the pixel of the mineral map is labeled as calcite (410). If the corresponding pixel of an element map for potassium has an element value greater than a certain threshold value, the pixel of the mineral map is labeled as KSpar (411). If the corresponding pixel of an element map for potassium has an element value greater than a certain threshold value, and if the corresponding pixel of an element map for aluminum has an element value greater than a certain threshold value, the pixel of the mineral map is labeled as illite (412). If the corresponding pixel of an element map for aluminum has an element value greater than a certain threshold value and if potassium is absent, the pixel of the mineral map is labeled as kaolinite (413). If the corresponding pixel of an element map for aluminum has an element value greater than a certain threshold value, the pixel of the mineral map is labeled as smectite (414). If the corresponding pixel of an element map for silicon has an element value greater than a certain threshold value, the pixel of the mineral map is labeled as quartz (415). Otherwise, the pixel of the mineral map is labeled as unclassified (416). Other threshold values can be used, as appropriate. In addition or in the alternative, other elements and minerals may be used with the example process of FIG. 4 including, but not limited to, those described before. In some embodiments, the sequence of analysis may different depending on the analyzed elements or depending on the threshold parameters used.

As explained previously, process 100 uses thresholds to determine (103) a presence of a substance, such as a mineral or organic substance, in a rock sample. Other processes may be used for analyzing a rock sample to make this determination. For example, if the gray-scale value of a BSE image corresponding to a pixel is less than a certain threshold, the pixel of the mineral map may be labeled as organics/pore. If a sample area corresponding to the pixel is determined to contain iron and sulfur, the pixel of the mineral map may be labeled as pyrite. If a sample area corresponding to the pixel is determined to contain potassium, aluminum, silicon, and amounts of magnesium and iron less than a certain threshold, the pixel of the mineral map may be labeled as illite. If a sample area corresponding to the pixel is determined to contain aluminum (and, in some embodiments, contain amounts of titanium greater than a certain threshold), the pixel of the mineral map may be labeled as smectite. If a sample area corresponding to the pixel is determined to contain aluminum and silicon, the pixel of the mineral map may be labeled as kaolinite. If a sample area corresponding to the pixel is determined to contain magnesium and contains amounts of calcium less than a certain threshold, the pixel of the mineral map may be labeled as dolomite. If a sample area corresponding to the pixel is determined to contain amounts of phosphorous and calcium greater than a certain threshold, the pixel of the mineral map may be labeled as apatite. If a sample area corresponding to the pixel is determined to contain calcium and sulfur, the pixel of the mineral map is labeled may be anhydrite. If a sample area corresponding to the pixel is determined to contain amounts of titanium greater than a certain threshold, the pixel of the mineral map may be labeled as anatase. If a sample area corresponding to the pixel is determined to contain amounts of silicon greater than a certain threshold, the pixel of the mineral map may be labeled quartz; and if the pixel is determined to contain calcium, the pixel of the mineral map may be labeled as calcite.

Figure 5:
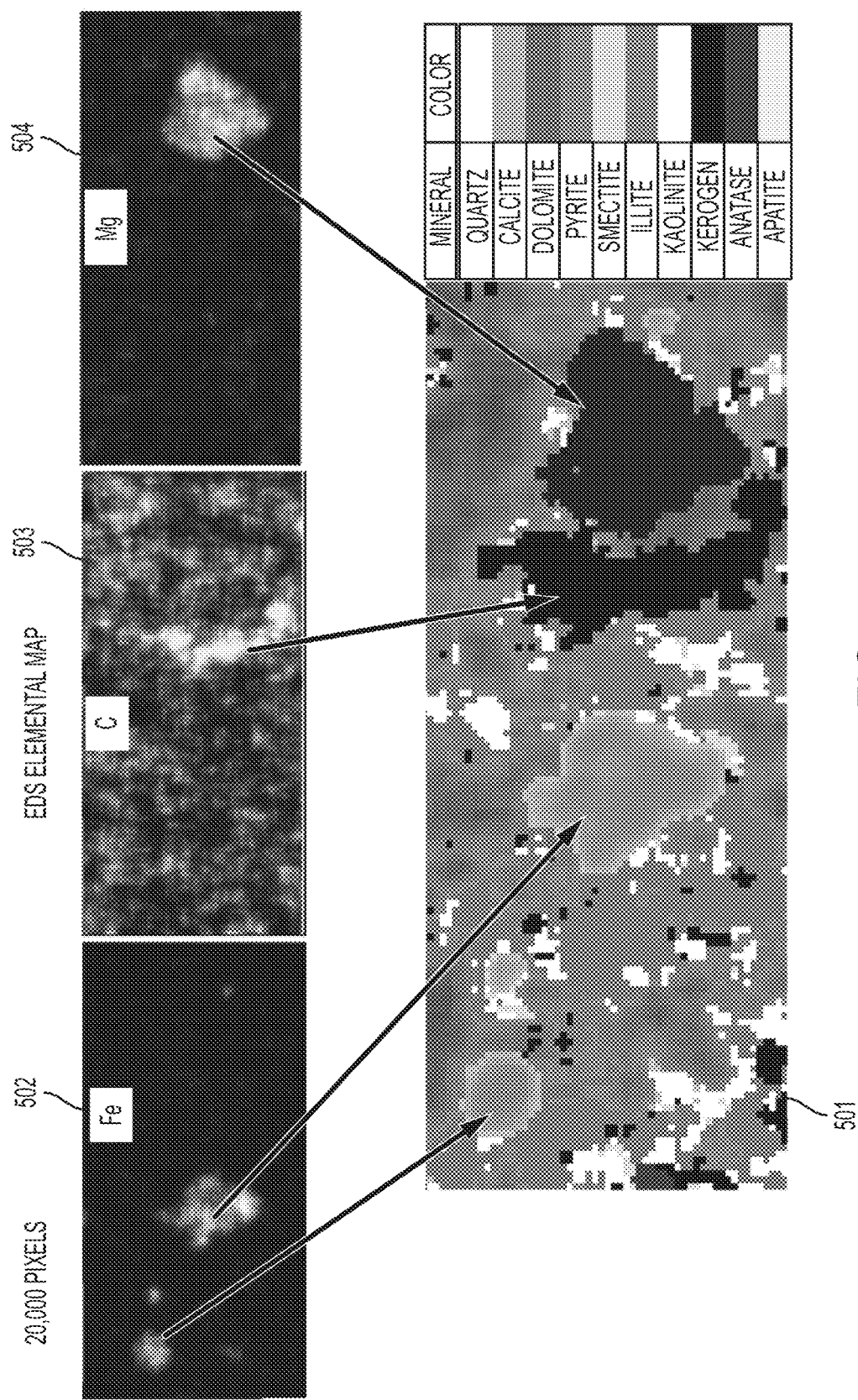
FIG. 5 shows an example mineral map and three EDS element maps.

FIG. 5 shows an example mineral map 501 obtained using example process 100. Mineral map 501 is a composite of image data from three elements, namely iron (Fe), carbon (C), and magnesium (Mg). In this example, the process of FIG. 3 identifies, in the subject rock sample, the presence of each of these elements in an appropriate element map 502, 503, or 504. Due to the presence of these elements, the process determines the mineralogical composition of the sample, including what minerals are in the sample and where they are located. In this example, mineral map 501 represents the different minerals using color; however, any appropriate distinguishing characteristic or attribute may be used to represent different minerals. For example, in FIG. 5, red shading is used to represent pyrite.

Figure 6:
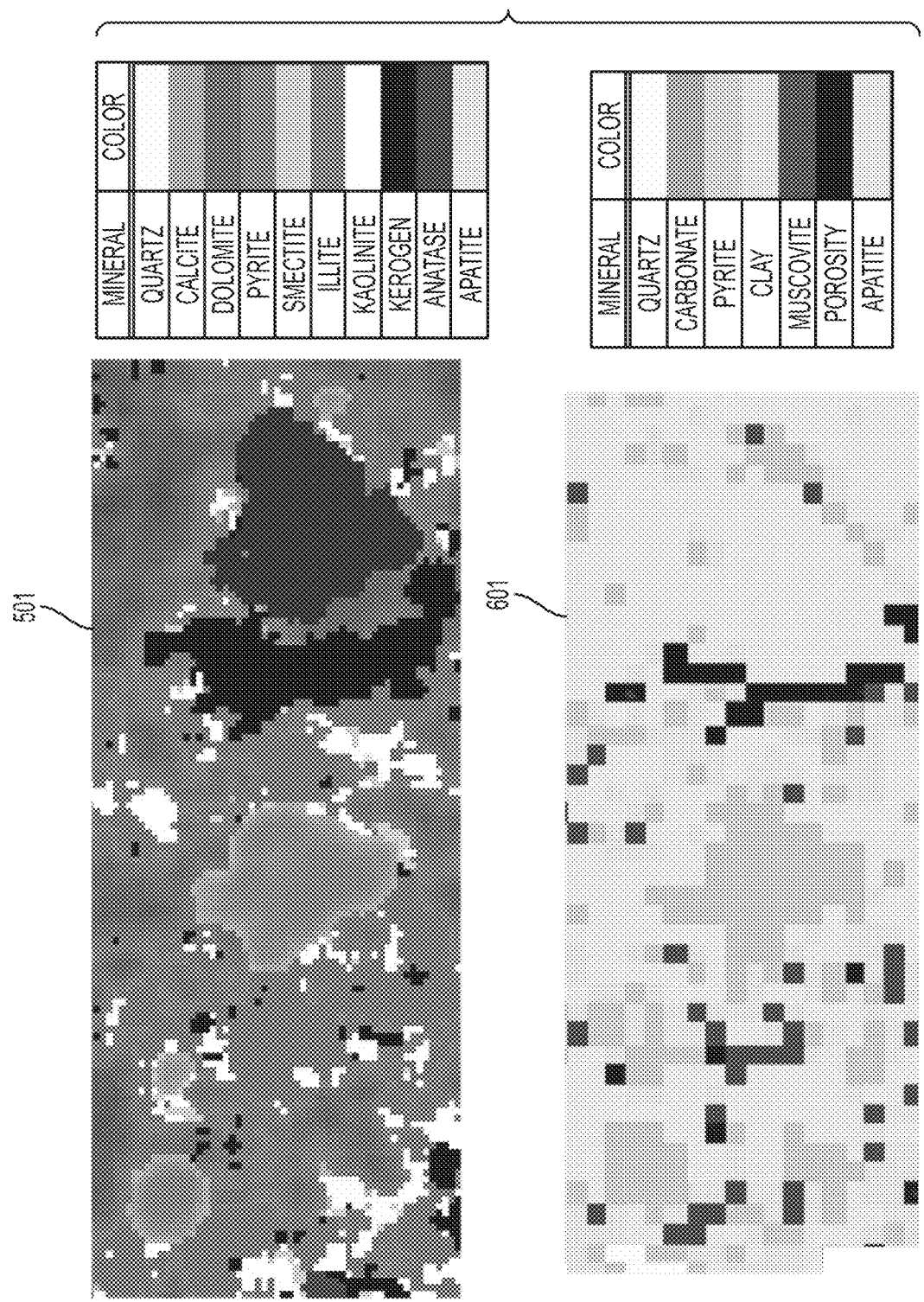
FIG. 6 shows the mineral map of FIG. 5 compared to a low-resolution mineral map for a same sample.

FIG. 6 shows the mineral map 501 of FIG. 5 compared to a low-resolution mineral map for a same sample 601. In this example, mineral map 501 is at a nano-scale resolution. As a result, mineral map 501 contains a relatively fine-grained topology and quantification for the rock sample. By contrast, low-resolution mineral map 601 does not provide the same amount of detail as mineral map 501. Low-resolution mineral map 601 is a type of mineral map that may be generated using processes other than those described in this document.

In some implementations, mineral maps that are generated using the example processes can be further refined or updated in response to user input. For example, FIG. 7A shows a refined version 701 of mineral map 501. In the example of FIG. 7A, the pyrite regions 702 and dolomite region 703 are updated relative to mineral map 501 of FIG. 5, and are more clearly delineated relative to the lower-resolution image shown in FIG. 7B.

Figure 8:
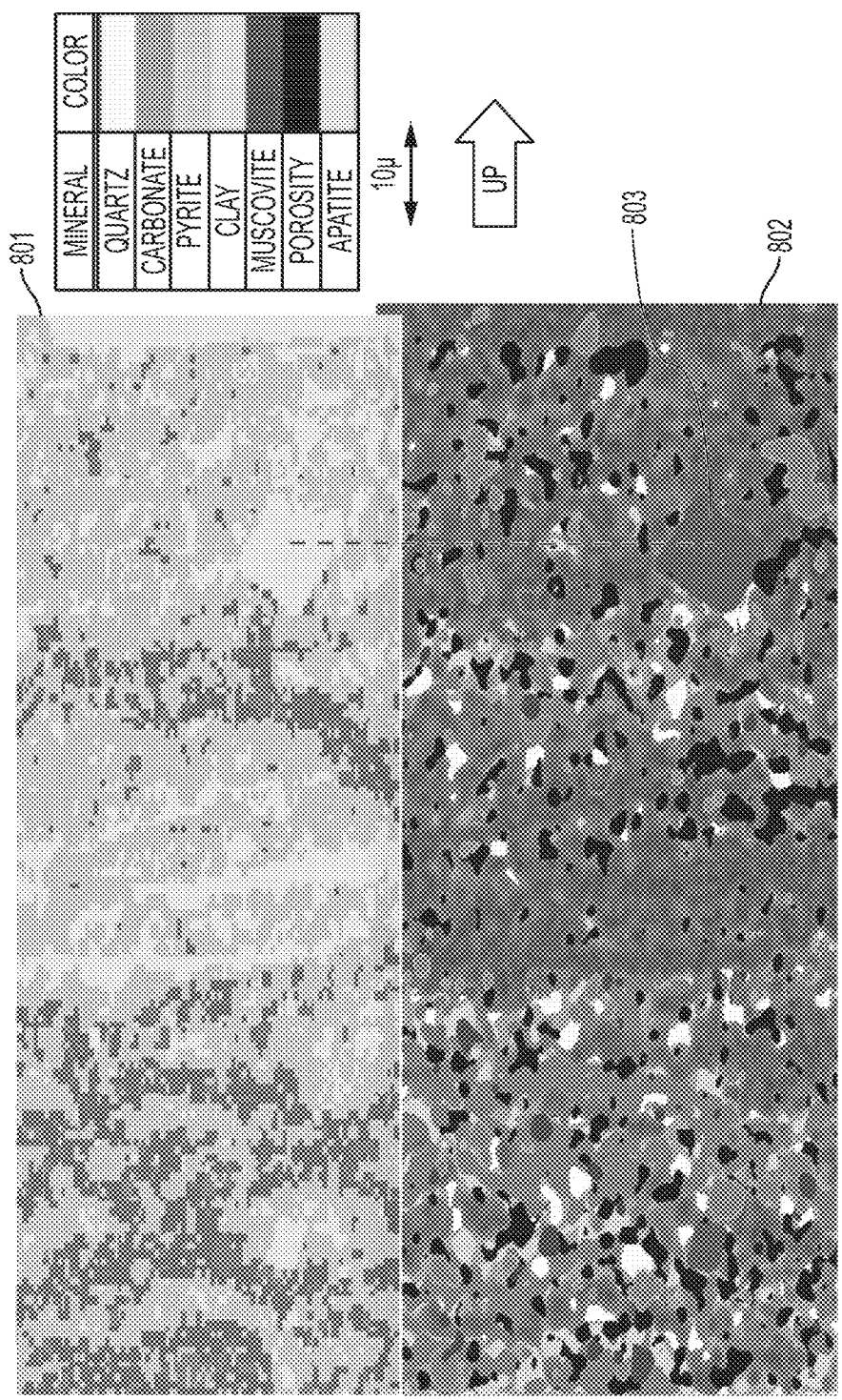
FIG. 8 shows an example low-resolution mineral map of a sample (top), and an example higher-resolution mineral map of the same sample (bottom).

FIG. 8 shows the contrast in resolution between a known low-resolution mineral map 801 and a mineral map 802 of the same section obtained using example process 100. Note that, in this example, the mineral map 802 shows a region of dolomite 803. As shown, image 801—the known, low-resolutions image—does not identify the dolomite region 803, but instead labels the same region as carbonate, which refers to lithology instead of a mineral.

Figure 9:
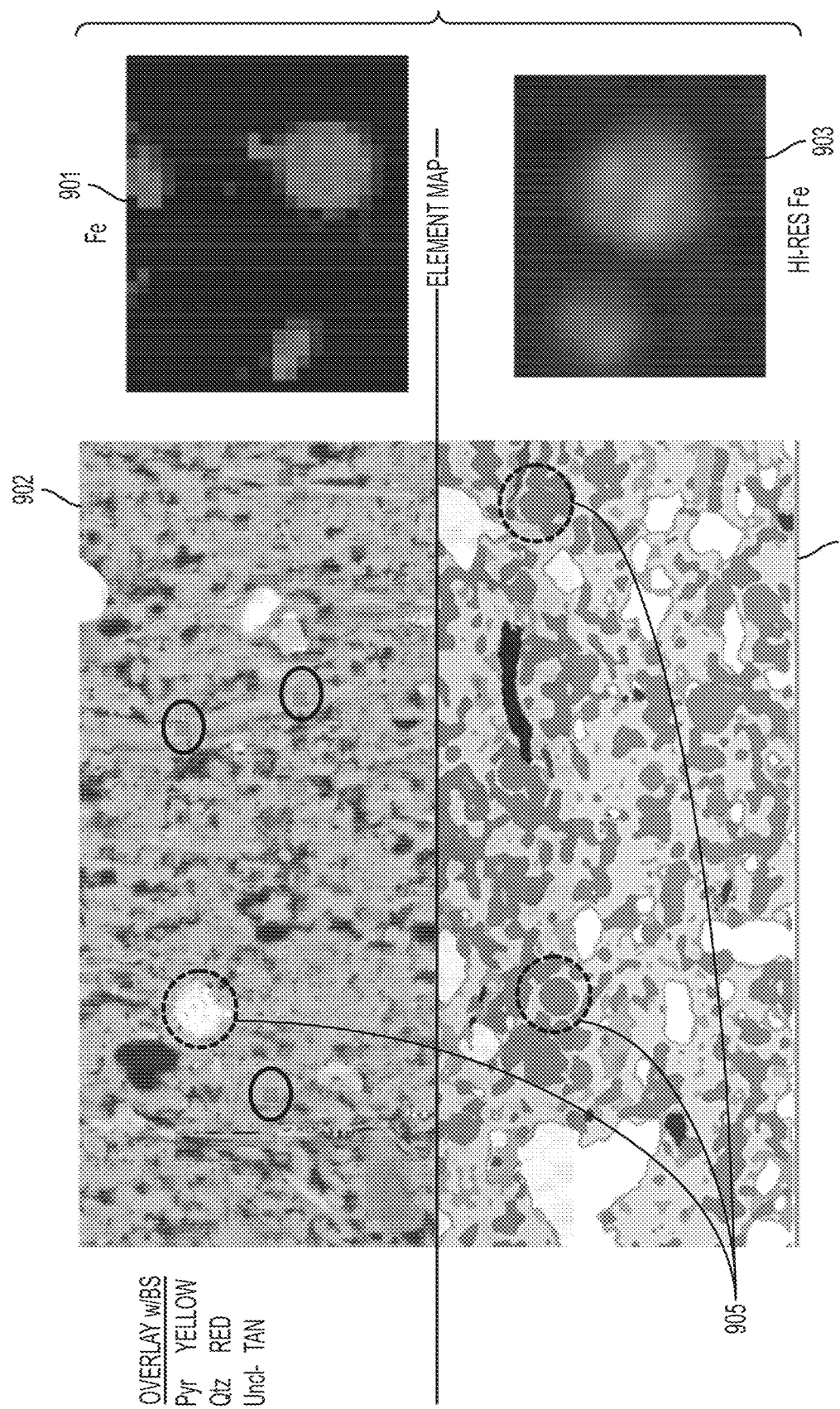
FIG. 9 shows an example mineral map and an example low-resolution element map for an iron sample (top), and an example mineral map and an example element map for the iron sample (bottom).

FIG. 9 shows the contrast in resolution between sample image 901 for iron and a known, low-resolution mineral map 902, and a sample image 903 for iron and a mineral map 904 generated using example process 100. In this example, small regions of iron 905 are clearly delineated in mineral map 904, while those same areas are ill-defined in image 902.

Figure 10:
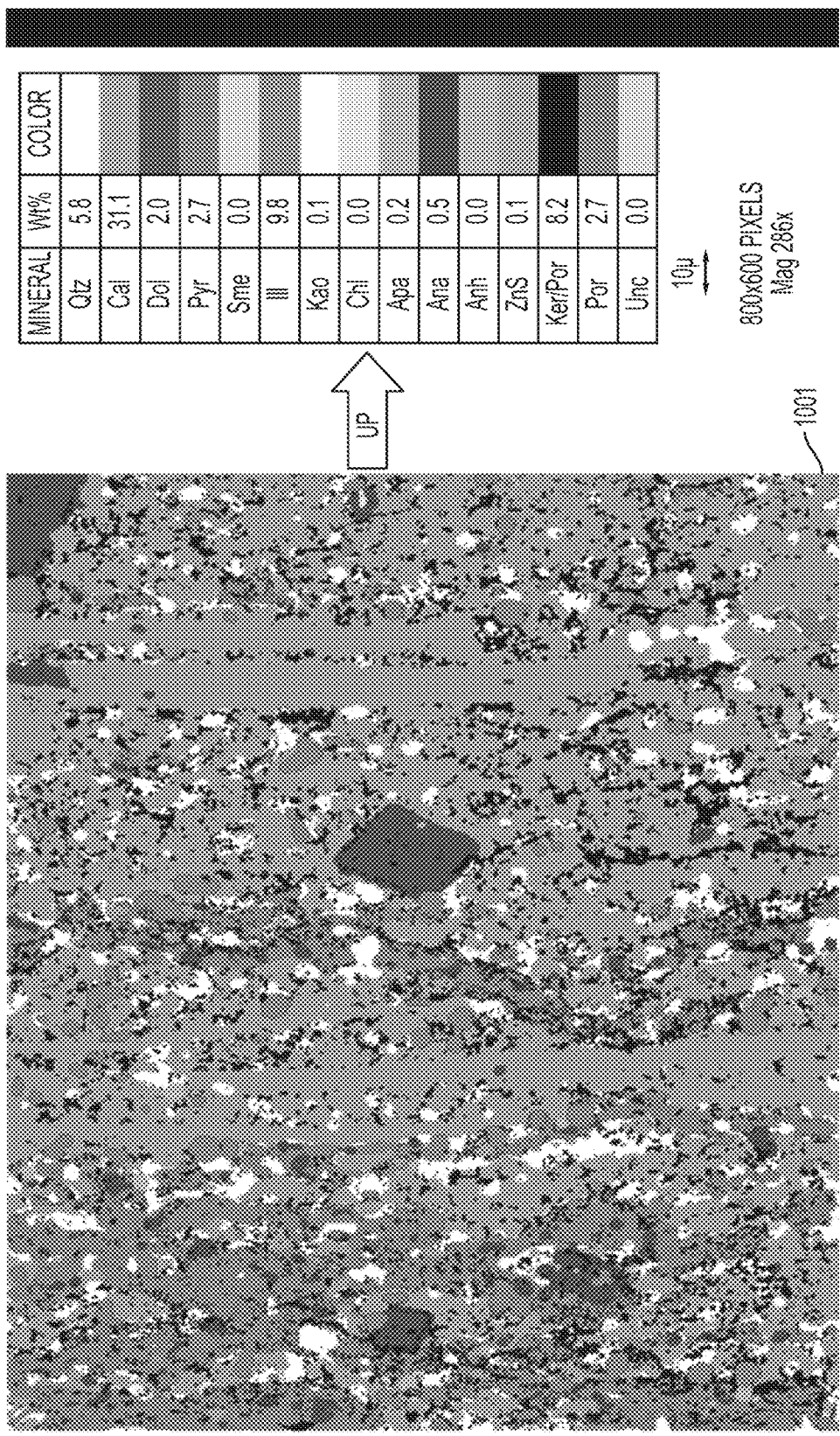
FIG. 10 shows an example mineral map.

FIG. 10 shows a mineral map 1001 obtained using example process 100. In some implementations, mineral amounts in mineral maps generated using process 100 are determined by calculating an area occupied by a certain mineral in a material map relative to a total area of the mineral map. In some implementations, mineral locations in mineral maps generated using process 100 are determined by examining the topology of the mineral map. This mineral map shown in FIG. 10 includes a layered structure of the imaged rock sample, which may have implications for characterization and assessment of the rock, for example in terms of the rock sedimentation or mechanical properties of the rock.

Figure 11:
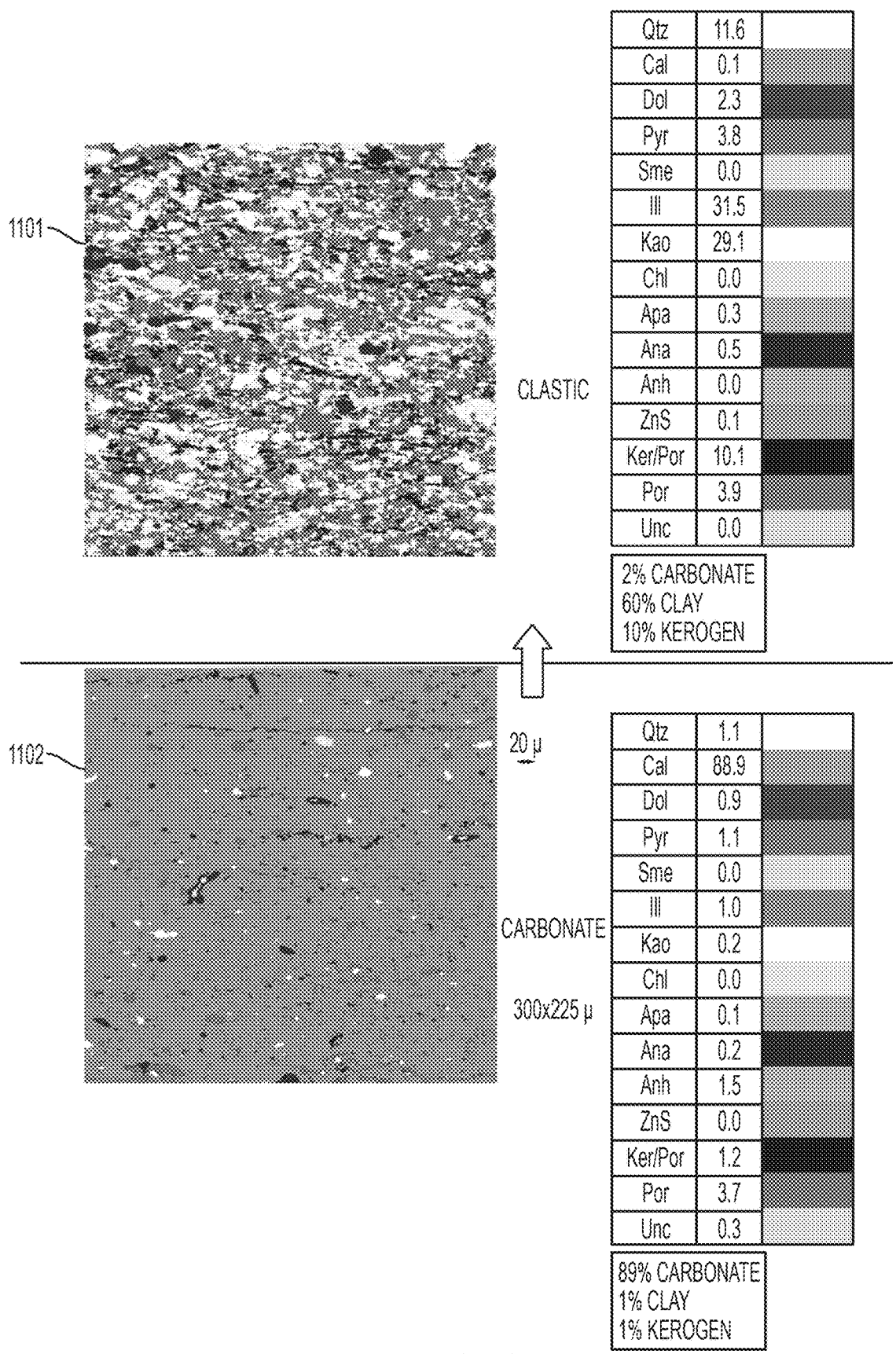
FIG. 11 shows an example mineral map of a clastic rock sample (top), and an example mineral map of carbonate rock (bottom).

FIG. 11 shows the contrast between a mineral map 1101 of clastic rock and a mineral map 1102 of carbonate rock obtained using example process 100.

Figure 12:
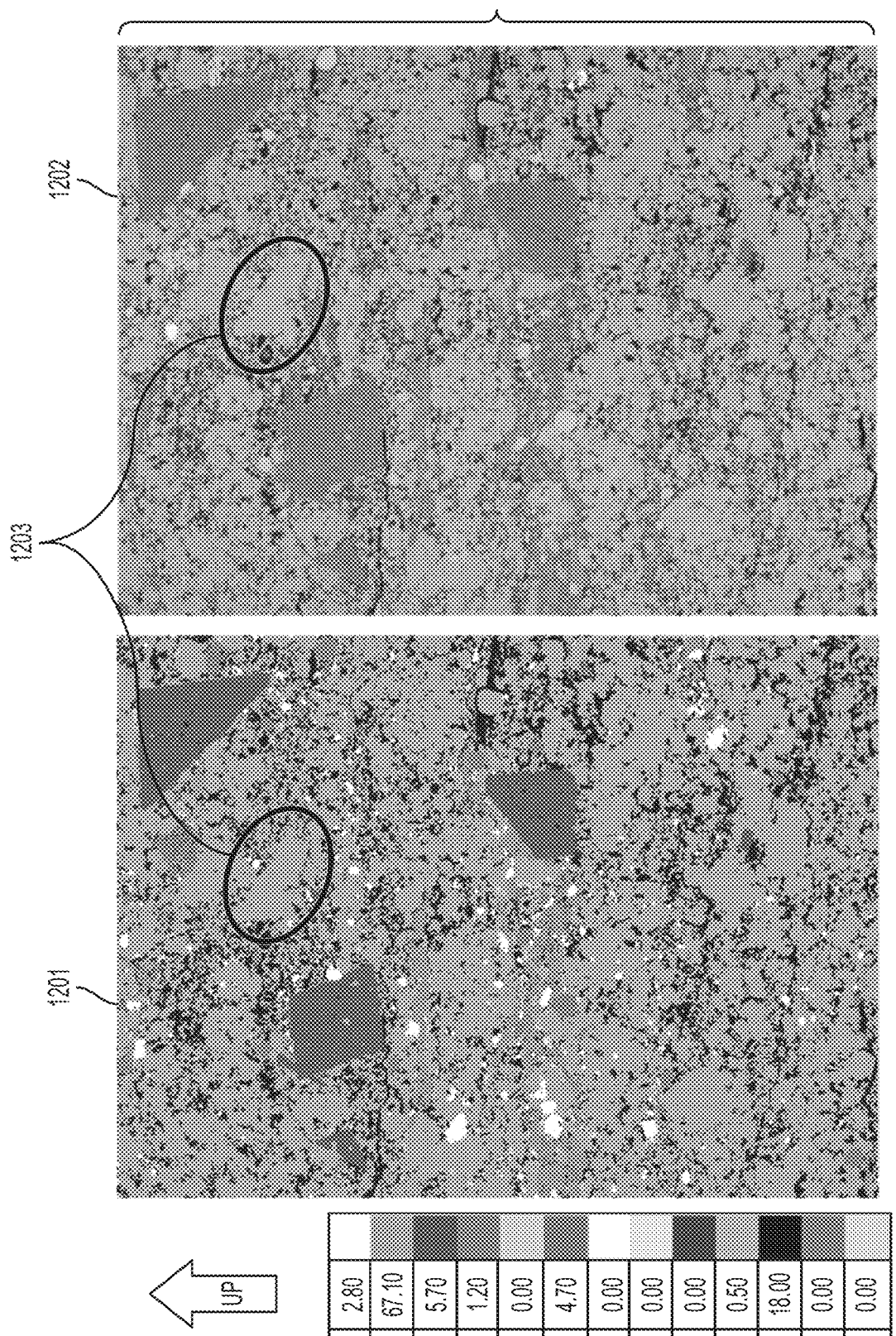
FIG. 12 shows an example mineral map (left), and the mineral map overlaid with a corresponding BSE image (right).

FIG. 12 shows a mineral map 1201 obtained using example process 100, and the same image with an overlay of a corresponding BSE image 1202. In some implementations, this overlay can enhance the definition of individual grains. An example of this enhanced definition is shown by the grain inside circled area 1203.

Figure 13A:
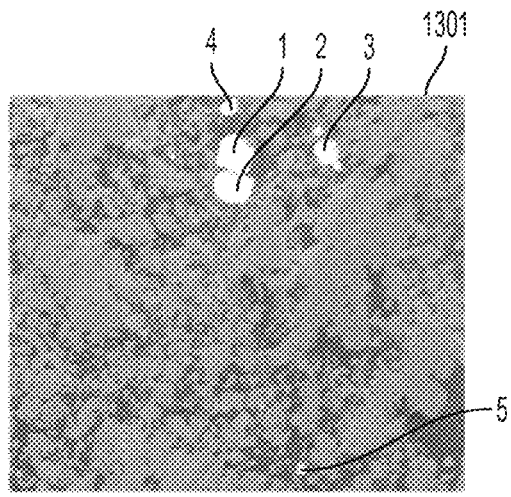
FIGS. 13A to 13C shows various types of SEM-derived images of a same sample.
Figure 13B:
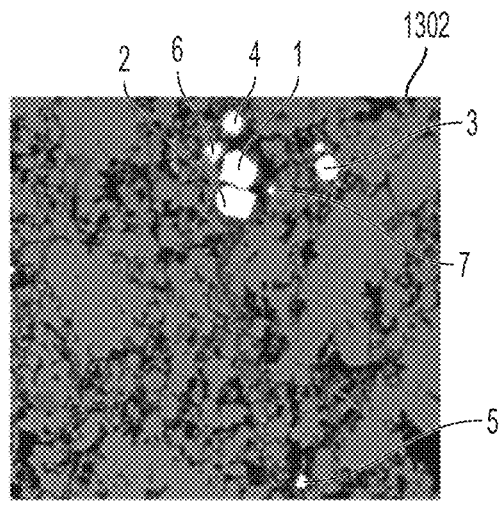
Figure 13C:
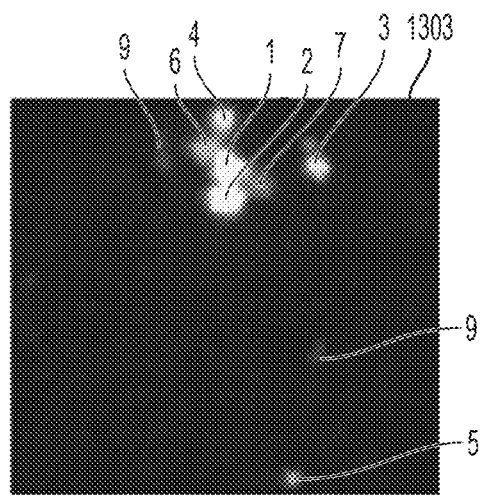
Figure 13D:
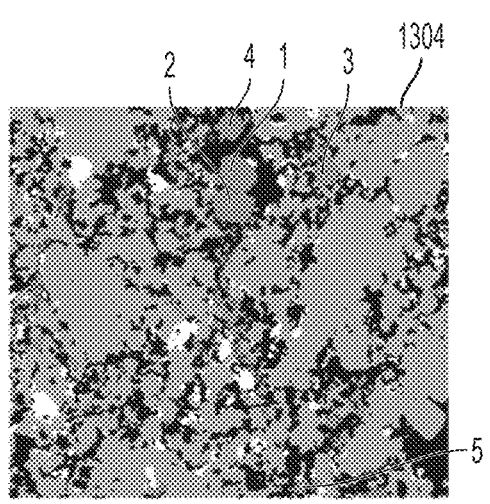
FIG. 13D shows a mineral map derived from the images in FIGS. 13A to 13C.
Figure 13E:
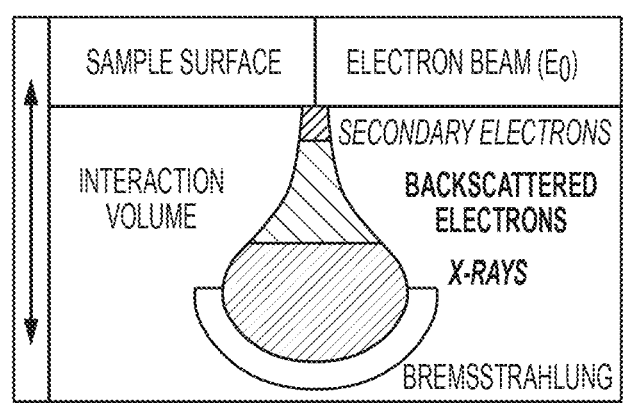
FIG. 13E shows a diagram of an interaction volume of a sample.

FIGS. 13A to 13C show various types of SEM-derived images that may be used in conjunction with example process 100. FIG. 13A shows a secondary electron (SE) image 1301 of a surface of a rock sample. In this example, there are five pyrite crystals, labeled 1 to 5. Secondary electrons are emitted from the shallowest region of the interaction volume, that is, the volume of a sample emitting detectable signals when subjected to an electron beam (see FIG. 13E). FIG. 13B shows a BSD image 1302 of the same region. Because backscattered electrons are emitted from a deeper region of the interaction volume, seven pyrite crystals can be detected. FIG. 13C shows an X-ray image (EDS image) 1303 of the same sample—in this case, in the form of an element map for iron (pyrite is formed from sulfur and iron). Because X-rays are emitted from an even deeper region of the interaction volume, nine pyrite crystals can be detected. FIG. 13D shows a mineral map 1304 generated from EDS images using example process 100. In this example, the input data was normalized on a scale from 0-255, with 255 being the highest intensity in an element map. Pyrite regions 6-9 have relatively low intensities (element values) and may be removed from the mineral map by controlling, for example, the display threshold of the mineral map. This effectively decreases the interaction volume. Thus, only pyrite regions 1 to 5 are shown in the mineral map, which resembles more closely the secondary electron map.

Figure 14:
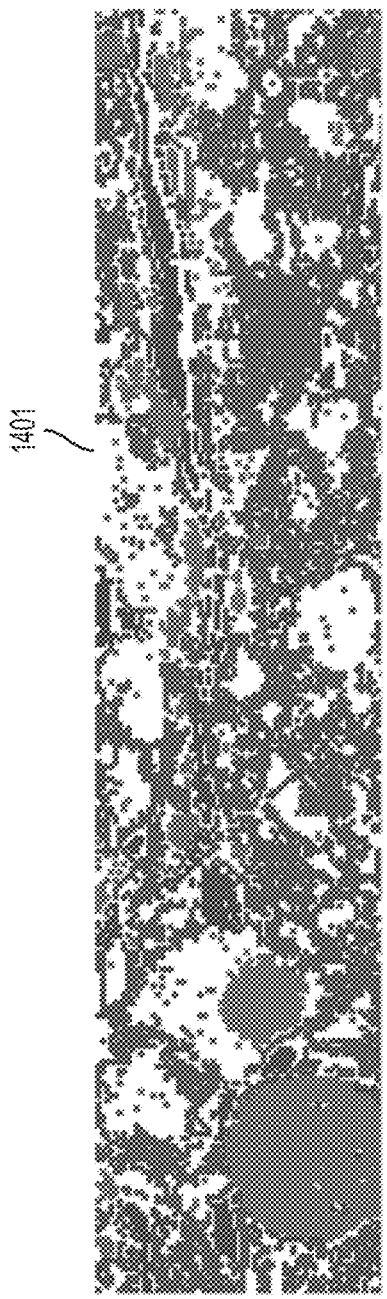
FIG. 14 shows an example mineral map generated from sample BSE data.

In some implementations, the example processes can also use BSE images alone or in combination with EDS and to identify minerals based on difference in gray-scale and "Z" (atomic number) values to further resolve grain boundaries and mineral spatial relationships. For example FIG. 14 shows an example mineral map 1401 generated solely from BSE data, using "Z" values to determine mineralogy.

Figure 15A:
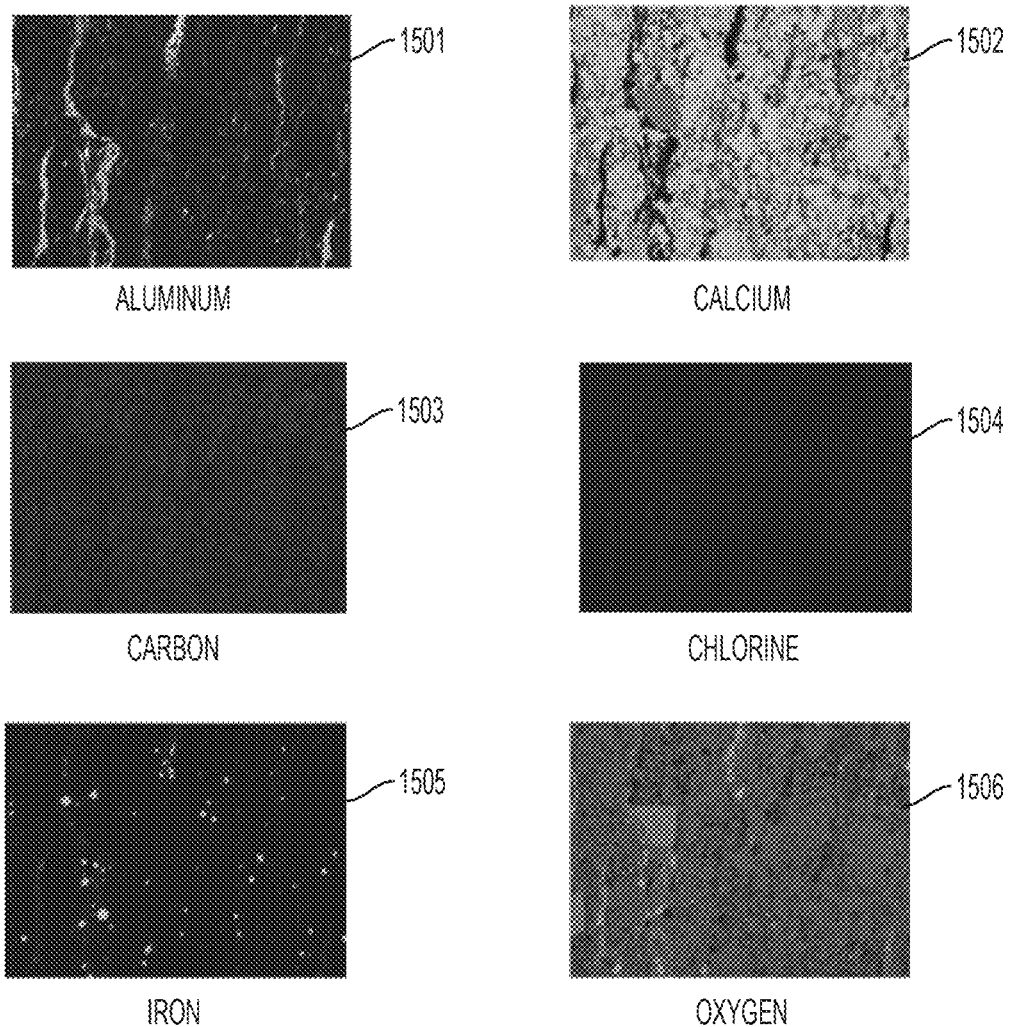
FIG. 15A shows example element maps for aluminum, calcium, carbon, chlorine, iron, and oxygen.
Figure 15B:
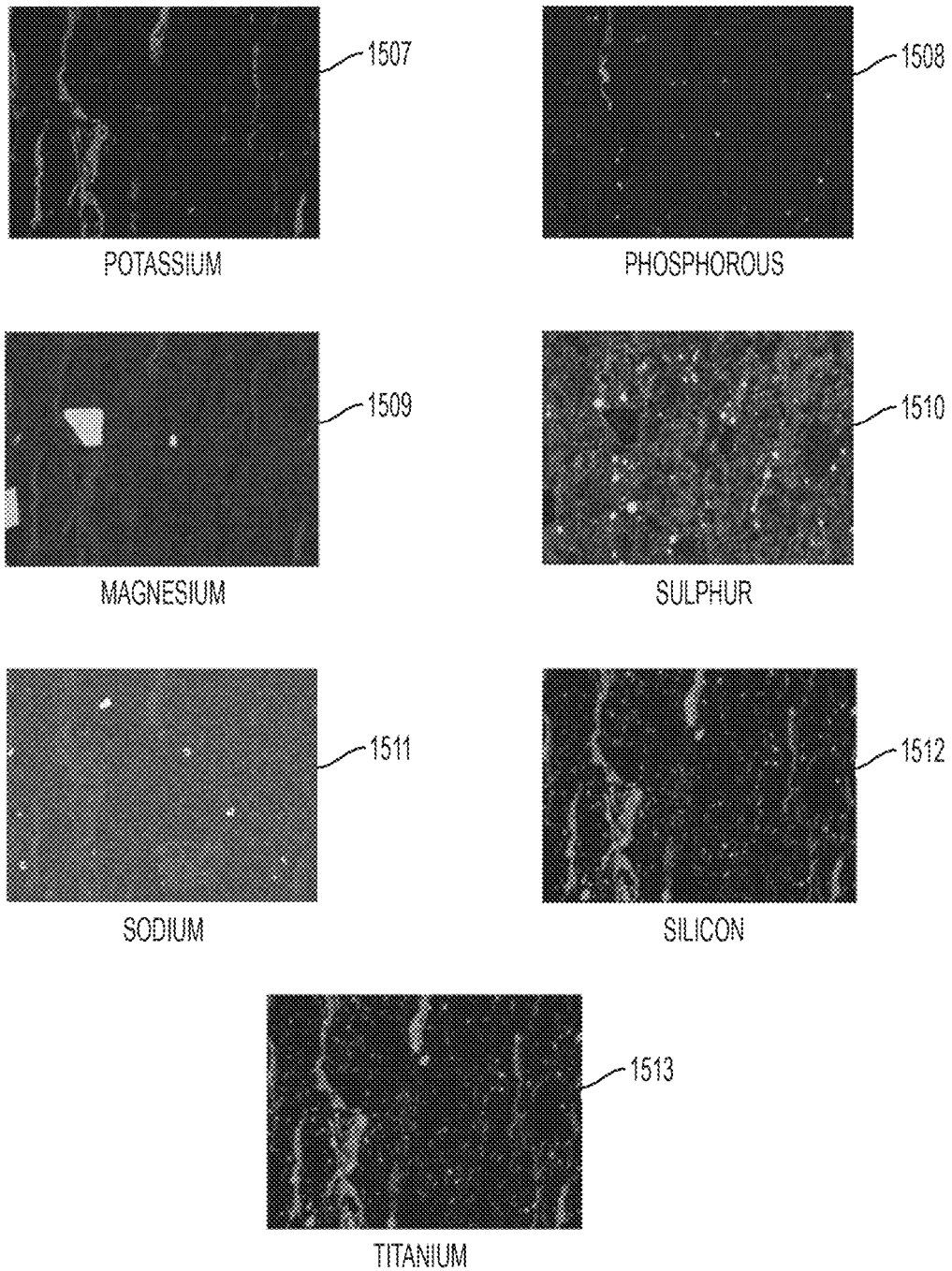
FIG. 15B shows example element maps for potassium, phosphorous, magnesium, sulfur, sodium, silicon, and titanium.

FIG. 15A shows example element map images for aluminum 1501, calcium 1502, carbon 1503, chlorine 1504, iron 1505, and oxygen 1506. FIG. 15B shows example element map images for potassium 1507, phosphorous 1508, magnesium 1509, sulfur 1510, sodium 1511, silicon 1512, and titanium 1513. A combined data set of the maps in FIG. 15 is shown in FIG. 16.

Figure 17A:
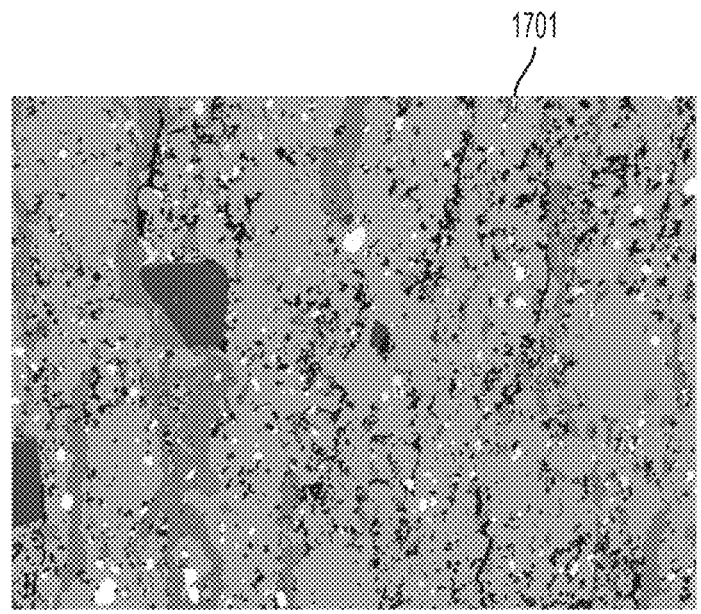
FIG. 17A shows an example mineral map for a sample.
Figure 17B:
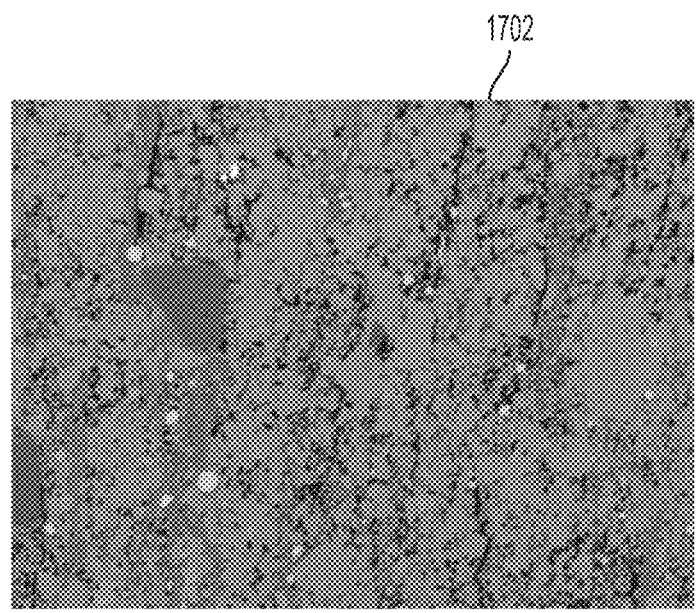
FIG. 17B shows the mineral map of FIG. 17A overlaid with a BSE image.

FIG. 17A shows an example mineral map 1701. Because a mineral map generally does not show textures in the way that a BSE image does, a degree of transparency can be added to the mineral map, and the image may be overlaid with the BSE image. This may provide more details concerning shapes, and may be used to perform a 'sanity check' to evaluate accuracy of that the mineral map. The overlay map 1702 is shown in FIG. 17B. In FIG. 17B, where the shapes of the minerals correlate well with the features on the BSE. This may indicate that the chosen thresholds for determination of elemental presence were correct.

In addition to, or instead of, SEM imaging techniques, the example processes may also be used with a variety of other imaging techniques. For example, the processes can be applied to perform mineral quantification using images generated using micro-X-ray fluorescence (micro-XRF) or Fourier transform infrared spectroscopy (FTIR).

In some implementations, the processes can be used to determine a likelihood of hydrocarbons in the rock sample and can be used for characterization of the substances and affecting operation of a hydrocarbon extraction process based on the likelihood of hydrocarbons in the rock sample.

For example, a certain mineral composition in the rock can indicate susceptibility of the rock to drilling or fracking, and may affect processes for drilling or fracking (for example, whether and where to perform those processes to extract hydrocarbons).

In some implementations, an automated threshold determination system may be implemented, since thresholds and other parameters may vary between samples or chemical element detection methods. For example, an automated threshold determination system may use the minimum, maximum, or average intensity for each of the elemental maps to guide the determination of threshold values for the processes. In some implementations, a neural network may be used to guide the processes to recognize what thresholds should be used in each case. For example, the guidance may be based on thresholds used previously for similar material. For example, if the processes detect an image that resembles images of other shales previously analyzed, the processes can identify the image as 'shale' and use threshold values from similar images. The same principles could be applied to other types of materials, as appropriate.

All or part of the processes described in this specification and their various modifications can be implemented, at least in part, via a computer program product, for example a computer program tangibly embodied in one or more information carriers, for example in one or more tangible machine-readable storage media, for execution by, or to control the operation of, data processing apparatus, for example a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as special purpose logic circuitry, for example an FPGA (field programmable gate array) or an ASIC (application-specific integrated circuit), or both.

Processors suitable for the execution of a computer program include, by way of example, both general and special purpose microprocessors, and any one or more processors of any kind of digital computer. Generally, a processor will receive instructions and data from a read-only storage area or a random access storage area or both. Components of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, for example magnetic, magneto-optical disks, or optical disks. Non-transitory machine-readable storage media suitable for embodying computer program instructions and data include all forms of non-volatile storage area, including by way of example, semiconductor storage area devices, for example erasable programmable read-only memory (EPROM), electrically erasable programmable read-only memory (EEPROM), and flash storage area devices; magnetic disks, for example internal hard disks or removable disks; magneto-optical disks; and CD-ROM and DVD-ROM disks.

Each computing device, such as a tablet computer, may include a hard drive for storing data and computer programs, and a processing device (for example a microprocessor) and memory (for example RAM) for executing computer programs. Each computing device may include an image capture device, such as a still camera or video camera. The image capture device may be built-in or simply accessible to the computing device.

Each computing device may include a graphics system, including a display screen. A display screen, such as a liquid crystal display (LCD) or a CRT (Cathode Ray Tube) displays, to a user, images that are generated by the graphics system of the computing device. As is well known, display on a computer display (for example a monitor) physically transforms the computer display. For example, if the computer display is LCD-based, the orientation of liquid crystals can be changed by the application of biasing voltages in a physical transformation that is visually apparent to the user. As another example, if the computer display is a CRT, the state of a fluorescent screen can be changed by the impact of electrons in a physical transformation that is also visually apparent. Each display screen may be touch-sensitive, allowing a user to enter information onto the display screen via a virtual keyboard. On some computing devices, such as a desktop or smartphone, a physical QWERTY keyboard and scroll wheel may be provided for entering information onto the display screen. Each computing device, and computer programs executed on such a computing device, may also be configured to accept voice commands, and to perform functions in response to such commands. For example, the process described in this specification may be initiated at a client, to the extent possible, via voice commands.

Components of different implementations described in this specification may be combined to form other implementations not specifically set forth in this specification. Components may be left out of the processes, computer programs, databases, etc. described in this specification without adversely affecting their operation. In addition, the logic flows shown in the figures do not require the particular order shown, or sequential order, to achieve desirable results. Various separate components may be combined into one or more individual components to perform the functions described here.

The patent or application file contains at least one drawing executed in color. Copies of this patent or patent application publication with color drawing(s) will be provided by the Office upon request and payment of the necessary fee.

What is claimed is:

1. A method for analyzing rock from an image of a sample region of the rock, the method comprising:
   accessing, by one or more processing devices, element maps of the sample region in a database, each element map comprising an array of pixels, and each pixel having a value that represents how closely the pixel correlates to a chemical element;
   accessing, by one or more processing devices, a database storing threshold values for multiple chemical elements including the chemical element;
   determining, by one or more processing devices, a presence of a substance in a portion of the sample region corresponding to the pixel by determining whether a value of the pixel in each of the element maps is greater than, or less than, a threshold value for a corresponding chemical element by selecting an element map for a chemical element;
comparing a value of the pixel in the selected element map to a first threshold; and
detecting the presence of a substance by determining if the value of the pixel has a predetermined relationship with the first threshold;
where, if the value of the pixel does not have the predetermined relationship with first threshold, the method further comprises repeating selecting, comparing, and determining for a different chemical element;
labeling, by one or more processing devices, the pixel based on the presence of the substance in the pixel; and
outputting, by one or more processing devices, data representing a substance map for rendering on a graphical interface.

2. The method of claim 1, where the image is obtained using scanning electron microscopy (SEM).

3. The method of claim 1, where at least one element map is generated based on a back scatter electron (BSE) image, an energy dispersive spectroscopy (EDS) image, a wave dispersive spectroscopy (WDS), or micro-X-ray fluorescence (micro-XRF) image.

4. The method of claim 1, where each element map is based on unprocessed image data.

5. The method of claim 1, where the chemical element comprises at least one of: aluminum, calcium, carbon, chlorine, iron, oxygen, potassium, phosphorous, magnesium, sulfur, sodium, silicon, or titanium.

6. The method of claim 1, where a resolution of the substance map is less than, or equal to, 250 nm per pixel.

7. The method of claim 1, where the predetermined relationship comprises the value of the pixel being greater than the first threshold.

8. The method of claim 1, where the predetermined relationship comprises the value of the pixel being less than the first threshold.

9. The method of claim 1, where determining comprises:
selecting an element map for a first chemical element;
comparing a value of the pixel in the selected element map to a first threshold;
determining that the value of the pixel has a first predetermined relationship with the first threshold;
selecting an element map for a second chemical element;
comparing a value of the pixel in the second selected element map to a second threshold; and
determining that the value of the pixel has a second predetermined relationship with the second threshold; and
where labeling comprises labeling the pixel as a substance based on the value of the pixel having the first predetermined relationship with the first threshold and based on the value of the pixel having the second predetermined relationship with the second threshold.

10. The method of claim 1, where the substance is a mineral, and where the substance map is a mineral map.

11. The method of claim 1, further comprising:
receiving data representing the sample region, the data being received from an imaging device and representing the pixel at a nano-scale resolution, the determining being based on the data received, the substance map being at a resolution that is based on the nano-scale resolution;
performing an assessment of substances in the substance map; and
outputting data that is based on the assessment.

12. The method of claim 11, where the data that is based on the assessment comprises a characterization of substances in the substance map.

13. The method of claim 12, further comprising:
determining a likelihood of hydrocarbons in the rock sample based on the characterization of the substances; and
affecting operation of a hydrocarbon extraction process based on the likelihood of hydrocarbons in the rock sample.

14. One or more non-transitory machine-readable storage media storing instructions for analyzing rock from an image of a sample region of the rock, the instructions being executable by one or more processing devices to perform operations comprising:
analyzing rock from an image of a sample region of the rock;
accessing element maps of the sample region in a database, each element map comprising an array of pixels, and each pixel having a value that represents how closely the pixel correlates to a chemical element;
accessing a database storing threshold values for multiple chemical elements including the chemical element;
determining a presence of a substance in a portion of the sample region corresponding to the pixel by determining whether a value of the pixel in each of the element maps is greater than, or less than, a threshold value for a corresponding chemical element by
selecting an element map for a chemical element;
comparing a value of the pixel in the selected element map to a first threshold; and
detecting the presence of a substance by determining if the value of the pixel has a predetermined relationship with the first threshold;
where, if the value of the pixel does not have the predetermined relationship with first threshold, the method further comprises repeating selecting, comparing, and determining for a different chemical element;
labeling the pixel based on the presence of the substance in the pixel; and
outputting data representing a substance map for rendering on a graphical interface.

15. The one or more non-transitory machine-readable storage media of claim 14, where the image is obtained using scanning electron microscopy (SEM).

16. The one or more non-transitory machine-readable storage media of claim 14, where at least one element map is generated based on a back scatter electron (BSE) image, an energy dispersive spectroscopy (EDS) image, a wave dispersive spectroscopy (WDS), or micro-X-ray fluorescence (micro-XRF) image.

17. The one or more non-transitory machine-readable storage media of claim 14, where each element map is based on unprocessed image data.

18. The one or more non-transitory machine-readable storage media of claim 14, where the chemical element comprises at least one of: aluminum, calcium, carbon, chlorine, iron, oxygen, potassium, phosphorous, magnesium, sulfur, sodium, silicon, or titanium.

19. The one or more non-transitory machine-readable storage media of claim 14, where a resolution of the substance map is less than, or equal to, 250 nm per pixel.

20. The one or more non-transitory machine-readable storage media of claim 14, where the predetermined relationship comprises the value of the pixel being greater than the first threshold.

21. The one or more non-transitory machine-readable storage media of claim 14, where the predetermined relationship comprises the value of the pixel being less than the first threshold.

22. The one or more non-transitory machine-readable storage media of claim 14, where determining comprises:
selecting an element map for a first chemical element;
comparing a value of the pixel in the selected element map to a first threshold;
determining that the value of the pixel has a first predetermined relationship with the first threshold;
selecting an element map for a second chemical element;
comparing a value of the pixel in the second selected element map to a second threshold; and
determining that the value of the pixel has a second predetermined relationship with the second threshold; and
where labeling comprises labeling the pixel as a substance based on the value of the pixel having the first predetermined relationship with the first threshold and based on the value of the pixel having the second predetermined relationship with the second threshold.

23. The one or more non-transitory machine-readable storage media of claim 14, where the substance is a mineral, and where the substance map is a mineral map.

24. The one or more non-transitory machine-readable storage media of claim 14, where the operations comprise:
receiving data representing the sample region, the data being received from an imaging device and representing the pixel at a nano-scale resolution, the determining being based on the data received, the substance map being at a resolution that is based on the nano-scale resolution;
performing an assessment of substances in the substance map; and
outputting data that is based on the assessment.

25. The one or more non-transitory machine-readable storage media of claim 24, where the data that is based on the assessment comprises a characterization of substances in the substance map.

26. The one or more non-transitory machine-readable storage media of claim 25, where the operations comprise:
determining a likelihood of hydrocarbons in the rock sample based on the characterization of the substances; and
affecting operation of a hydrocarbon extraction process based on the likelihood of hydrocarbons in the rock sample.

27. A system comprising:
one or more non-transitory machine-readable storage media storing instructions for analyzing rock from an image of a sample region of the rock; and
one or more processing devices to execute the instructions to perform operations comprising:
analyzing rock from an image of a sample region of the rock;
accessing element maps of the sample region in a database, each element map comprising an array of pixels, and each pixel having a value that represents how closely the pixel correlates to a chemical element;
accessing a database storing threshold values for multiple chemical elements including the chemical element;
determining a presence of a substance in a portion of the sample region corresponding to the pixel by determining whether a value of the pixel in each of the element maps is greater than, or less than, a threshold value for a corresponding chemical element by
selecting an element map for a chemical element
comparing a value of the pixel in the selected element map to a first threshold; and
detecting the presence of a substance by determining if the value of the pixel has a predetermined relationship with the first threshold;
where, if the value of the pixel does not have the predetermined relationship with first threshold, the method further comprises repeating selecting, comparing, and determining for a different chemical element;
labeling the pixel based on the presence of the substance in the pixel; and
outputting data representing a substance map for rendering on a graphical interface.

28. The system of claim 27, where the image is obtained using scanning electron microscopy (SEM).

29. The system of claim 27, where at least one element map is generated based on a back scatter electron (BSE) image, an energy dispersive spectroscopy (EDS) image, a wave dispersive spectroscopy (WDS), or micro-X-ray fluorescence (micro-XRF) image.

30. The system of claim 27, where each element map is based on unprocessed image data.

31. The system of claim 27, where the chemical element comprises at least one of: aluminum, calcium, carbon, chlorine, iron, oxygen, potassium, phosphorous, magnesium, sulfur, sodium, silicon, or titanium.

32. The system of claim 27, where a resolution of the substance map is less than, or equal to, 250 nm per pixel.

33. The system of claim 27, where the predetermined relationship comprises the value of the pixel being greater than the first threshold.

34. The system of claim 27, where the predetermined relationship comprises the value of the pixel being less than the first threshold.

35. The system of claim 27, where determining comprises:
selecting an element map for a first chemical element;
comparing a value of the pixel in the selected element map to a first threshold;
determining that the value of the pixel has a first predetermined relationship with the first threshold;
selecting an element map for a second chemical element;
comparing a value of the pixel in the second selected element map to a second threshold; and
determining that the value of the pixel has a second predetermined relationship with the second threshold; and
where labeling comprises labeling the pixel as a substance based on the value of the pixel having the first predetermined relationship with the first threshold and based on the value of the pixel having the second predetermined relationship with the second threshold.

36. The system of claim 27, where the substance is a mineral, and where the substance map is a mineral map.

37. The system of claim 27, where the operations comprise:
receiving data representing the sample region, the data being received from an imaging device and representing the pixel at a nano-scale resolution, the determining being based on the data received, the substance map being at a resolution that is based on the nano-scale resolution;
performing an assessment of substances in the substance map; and
outputting data that is based on the assessment.

38. The system of claim 37, where the data that is based on the assessment comprises a characterization of substances in the substance map.

39. The system of claim 38, where the operations comprise:
determining a likelihood of hydrocarbons in the rock sample based on the characterization of the substances; and
affecting operation of a hydrocarbon extraction process based on the likelihood of hydrocarbons in the rock sample.

* * * * *